(12) United States Patent
Deisseroth et al.

(10) Patent No.: US 10,495,554 B2
(45) Date of Patent: Dec. 3, 2019

(54) METHOD AND SYSTEM FOR IMAGING AND ANALYSIS OF A BIOLOGICAL SPECIMEN

(71) Applicant: The Board of Trustees of the Leland Stanford Junior University, Stanford, CA (US)

(72) Inventors: Karl A. Deisseroth, Stanford, CA (US); William E. Allen, Albany, CA (US); Brian Hsueh, Stanford, CA (US); Li Ye, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/605,728

(22) Filed: May 25, 2017

(65) Prior Publication Data
US 2018/0045622 A1 Feb. 15, 2018

Related U.S. Application Data

(60) Provisional application No. 62/341,377, filed on May 25, 2016.

(51) Int. Cl.
| | | |
|---|---|---|
| *G01N 1/30* | (2006.01) | |
| *G01N 1/31* | (2006.01) | |
| *B01L 3/00* | (2006.01) | |
| *G01N 33/483* | (2006.01) | |
| *G01N 33/50* | (2006.01) | |
| *G06K 9/00* | (2006.01) | |
| *G06T 7/00* | (2017.01) | |
| *G01N 33/53* | (2006.01) | |
| *G01N 1/34* | (2006.01) | |

(52) U.S. Cl.
CPC ............... *G01N 1/30* (2013.01); *B01L 3/502* (2013.01); *G01N 1/31* (2013.01); *G01N 33/4833* (2013.01); *G01N 33/5058* (2013.01); *G01N 33/5088* (2013.01); *G01N 33/53* (2013.01); *G06K 9/0014* (2013.01); *G06T 7/0014* (2013.01); *B01L 2200/026* (2013.01); *B01L 2200/16* (2013.01); *B01L 2300/0609* (2013.01); *B01L 2300/0832* (2013.01); *G01N 1/34* (2013.01); *G01N 2001/305* (2013.01); *G06T 2207/10056* (2013.01); *G06T 2207/30016* (2013.01); *G06T 2207/30024* (2013.01)

(58) Field of Classification Search
CPC ......... G01N 1/30; G01N 1/31; G01N 33/4833
See application file for complete search history.

(56) References Cited

U.S. PATENT DOCUMENTS

| | | | |
|---|---|---|---|
| 8,852,614 B2 | 10/2014 | Frank et al. | |
| 2010/0055733 A1 | 3/2010 | Lutolf et al. | |
| 2013/0031066 A1 | 1/2013 | Ducharme et al. | |
| 2015/0144490 A1* | 5/2015 | Deisseroth | G01N 1/30 204/461 |
| 2016/0131560 A1* | 5/2016 | Gradinaru | G01N 1/30 435/29 |
| 2017/0068086 A1 | 3/2017 | Tomer et al. | |

FOREIGN PATENT DOCUMENTS

| | | |
|---|---|---|
| WO | 2014025392 | 2/2014 |
| WO | 2015041755 | 3/2015 |

OTHER PUBLICATIONS

BioWORLD, 2018.*
Bevis and Glick (2002) "Rapidly maturing variants of the Discosoma red fluorescent protein (DsRed)" Nat. Biotechnol., 20:83-87.
Guenthner et al. (2013) "Permanent Genetic Access to Transiently Active Neurons via TRAP: Targeted Recombination in Active Populations" Neuron, 78(5):773-784.
Hern and Hubbell (1998) "Incorporation of adhesion peptides into nonadhesive hydrogels useful for tissue resurfacing" J. Biomed. Mater. Res., 39:266.
Huh and Bae (1999) "Synthesis and characterization of poly(ethylene glycol)/poly(l-lactic acid) alternating multiblock copolymers" Polymer, 40(22):6147-6155.
Klein et al. (2010) "elastix: A Toolbox for Intensity-Based Medical Image Registration" IEEE Trans Med Imaging, 29:196-205.
Lee et al. (2010) "Hydrophobic nanoparticles improve permeability of cell-encapsulating poly(ethylene glycol) hydrogels while maintaining patternability" Proc. Natl. Acad. Sci., 107(48):20709-20714.
Maintz and Viergever (1998) "A survey of medical Image Registration" Medical Image Analysis, 2:1-36.
Matz et al. (1999) "Fluorescent proteins from nonbioluminescent Anthozoa species" Nature Biotechnology, 17:969-973.
Nagai et al. (2002) "A variant of yellow fluorescent protein with fast and efficient maturation for cell-biological application" Nat. Biotechnol., 20(1):87-90.
Nguyen and Daugherty (2005) "Evolutionary optimization of fluorescent proteins for intracellular FRET" Nat Biotechnol., 23(3)355-360.
Rizzo et al. (2004) "An improved cyan fluorescent protein variant useful for FRET" Nat Biotechnol., 22(4):445-449.
Sanz et al. (2009) "Cell-type-specific isolation of ribosome-associated mRNA from complex tissues" Proc Natl Acad Sci U S A, 106(33):13939-13944.

(Continued)

*Primary Examiner* — Ruth A Davis
(74) *Attorney, Agent, or Firm* — Edward J. Baba; Jenny Buchbinder; Bozicevic, Field & Francis LLP

(57) ABSTRACT

The present disclosure provides methods of preparing a biological specimen for imaging analysis, comprising fixing and clearing the biological specimen and subsequently analyzing the cleared biological specimen using microscopy. Also included are methods of quantifying cells, for example, active populations of cells in response to a stimulant. The present disclosure also provides devices for practicing the described methods. A flow-assisted clearing device provides rapid clearing of hydrogel-embedded biological specimens without the need of specialized equipment such as electrophoresis or perfusion devices.

29 Claims, 14 Drawing Sheets

(56) References Cited

OTHER PUBLICATIONS

Shaner et al. (2005) "A guide to choosing fluorescent proteins" Nat Methods. 2(12):905-909.
Shkrob et al. (2005) "Far-red fluorescent proteins evolved from a blue chromoprotein from Actinia equine" Biochem J., 392(3):649-654.
Tainaka et al. (2014) "Whole-Body Imaging with Single-Cell Resolution by Tissue Decolorization" Cell, 159 (4):911-924.
Wang et al. (2004) "Evolution of new nonantibody proteins via iterative somatic hypermutation" PNAS USA., 101 (48):16745-16749.
West and Hubbell (1999) "Polymeric Biomaterials with Degradation Sites for Proteases Involved in Cell Migration" Macromolecules, 32:241-244.
Wiedenmann et al. (2002) "A far-red fluorescent protein with fast maturation and reduced oligomerization tendency from Entacmaea quadricolor (Anthozoa, Actinaria)" Proc Natl Acad Sci USA., 99(18):11646-11651.

\* cited by examiner

METHOD AND SYSTEM FOR IMAGING AND ANALYSIS OF A BIOLOGICAL SPECIMEN

CROSS-REFERENCE TO RELATED APPLICATIONS

This application claims the benefit of U.S. Provisional Patent Application No. 62/341,377 filed May 25, 2016, which application is incorporated herein by reference in its entirety.

BACKGROUND

The many individual regions and layers of the mammalian prefrontal cortex are known to contain cells with a rich diversity of activity patterns. Indeed, otherwise-indistinguishable populations of principal cells exhibiting profoundly distinct changes in activity in response to the same task or stimulus have been characterized by electrophysiological recording and cellular-resolution fluorescence $Ca^{2+}$ imaging. At the same time, datastreams of anatomical and molecular information on prefrontal cell typology have emerged from a variety of methods, also pointing toward rich cellular diversity of principal excitatory neurons. Together these findings have highlighted the morphological, wiring, and electrophysiological diversity of principal neurons even within individual layers and subregions.

The mapping and correspondences among different domains of diversity (e.g., activity during behavior, long-range wiring, and molecular phenotype) has fundamental implications for elucidating the cellular logic of prefrontal cortex function; moreover, differences in wiring, role in behavior, and molecular signatures among differentially-responsive cells could provide insight into the mechanisms of action of current neuromodulation therapies, and perhaps even lay the foundation for developing new kinds of cell-targeted disease treatment. The present disclosure provides an approach to quantify neuronal activity at the single cell level in intact brains, to assess the unique and non-stereotyped nature of the mammalian nervous system.

SUMMARY

Aspects of the present disclosure include a method of preparing a biological specimen for imaging analysis, the method comprising: fixing the biological specimen with a plurality of hydrogel monomers to produce a hydrogel-fixed specimen; clearing the hydrogel-fixed specimen using a flow-assisted clearing device to produce a cleared specimen, wherein the clearing is performed by: immersing the hydrogel-fixed specimen in a buffer; flowing the buffer through the hydrogel-fixed specimen, wherein the buffer flow is unidirectional; and contacting the cleared specimen with a refractive index matching solution prior to imaging analysis.

In other aspects, the method includes where the flow-assisted clearing device comprises: a sample chamber comprising an inlet and an outlet, wherein the inlet delivers the buffer into the sample chamber and the outlet draws the buffer out of the sample chamber; a sample holder, wherein the sample holder can be removably placed inside the sample chamber, and wherein the sample holder allows the buffer to flow through; and a buffer circulator.

In other aspects, the method includes where the buffer delivered by the inlet is fresh or is reused.

In other aspects, the method includes where the buffer circulator is a temperature-controlled circulator.

In other aspects, the method includes where the flow-assisted clearing device comprises: a container; a sample holder, wherein the sample holder allows the buffer to flow through, and wherein the sample holder can be removably placed inside the container; and a buffer circulator.

In other aspects, the method includes where the buffer circulator comprises a rotating rod. In some cases the rotating rod is a magnetic rotating rod and is controlled by an external magnetic field.

In other aspects, the method includes where a plurality of flow-assisted clearing devices are arranged in parallel to the buffer circulator. In some cases, each of the plurality of flow-assisted clearing devices clears a plurality of hydrogel-fixed specimens.

In other aspects, the flow-assisted clearing device is not an electrophoresis chamber.

In other aspects, the method includes where the flow-assisted clearing device further comprises a buffer filter component.

In other aspects, the method includes where the buffer circulator generates a unidirectional flow of the buffer through the sample holder.

In other aspects, the method includes where fixing the biological specimen comprises contacting the biological specimen with paraformaldehyde. In some cases, contacting the biological specimen with paraformaldehyde comprises transcardial perfusion.

In other aspects the method includes where the plurality of hydrogel monomers comprise acrylamide. For example, 1% acrylamide.

In other aspects the method includes where clearing the hydrogel-fixed specimen further comprises substantially removing a plurality of cellular components from the hydrogel-fixed specimen. In some cases the plurality of cellular components comprises lipids.

In other aspects the method includes where clearing the hydrogel-fixed specimen is performed at about 40° C.

In other aspects the method includes where the buffer comprises a Tris buffer and an ionic surfactant. In some cases, the Tris buffer is Tris-Boric buffer. In some cases, the ionic surfactant is sodium dodecyl sulfate. In some cases, the buffer is at about pH 8.5.

In other aspects the method includes where the refractive index matching solution has a refractive index that matches that of the cleared specimen. In some cases, the refractive index matching solution has a refractive index of 1.45. In some cases, the refractive index matching solution is RapidClear or FocusClear.

In other aspects the method includes where the biological specimen is a central nervous system tissue, a whole brain, or a whole spinal cord.

Aspects of the instant disclosure include a method for quantifying an active neuronal population of a subject animal exposed to a stimulant, the method comprising: delivering a stimulant to the subject animal; isolating the brain of the subject animal; preparing the brain of the animal according to any previous method to produce a cleared brain; imaging the cleared brain; and identifying the active neuronal population.

In other aspects the method includes incubating the cleared brain in a mounting medium prior to imaging. In some cases, the mounting medium is RapidClear Mounting Gel.

In other aspects the method includes where the active neuronal population of the animal is labeled. In some cases, the active neuronal population of the animal is labeled by targeted recombination in active populations (TRAP).

In other aspects the method includes administering a tamoxifen in an aqueous buffer containing DMSO and Tween 80, to induce targeted recombination in active populations. In some cases, the tamoxifen is 4-hydroxytamoxifen.

In other aspects the method includes where the step of identifying the active neuronal population comprises: illuminating the cleared brain with two light sheets from a first side and a second side to produce a sample image volume, wherein the second side is opposite to the first side; registering the sample image volume to a reference image volume; and identifying the active neuronal population from the registered sample image volume.

In other aspects the method includes where the native image volume is deconvolved.

In other aspects the method includes where the registering step comprises nonlinearly registering the sample image volume to the reference image volume to produce a nonlinear registration.

In other aspects the method includes where identifying the active neuronal population further comprises: identifying an active cell location in the sample image volume; and mapping the active cell location to the registered sample image.

In other aspects the method includes where the mapping step further comprises: generating a binary mask volume for a specified region in the nonlinear registration; and counting the number of active cells in the active cell location.

In other aspects the method includes where the specified region is manually specified. In some cases, the specified region comprises a pre-specified region from an Allen Brain Atlas image volume.

In other aspects the method includes where the reference image volume is generated by: globally aligning a plurality of image volumes obtained from a plurality of cleared brains to an Allen Brain Atlas image volume; and averaging the plurality of globally aligned image volumes.

In other aspects the method includes where the step of globally aligning comprises affine registration and/or spline registration.

In other aspects the method includes where the Allen Brain Atlas image volume is an Allen Brain Atlas Nissl-stained image volume.

In other aspects the method includes where the stimulant is amphetamine, caffeine, ephedrine, 3,4-methylenedioxymethamphetamine (MDMA), methylenedioxypyrovalerone (MDPV), prolintane, mephedrone, methamphetamine, nicotine, phenylpropanolamine, propylhexedrine, dimethylamylamine, pseudoephedrine, cathinone, or cocaine.

In other aspects the method includes where the stimulant generates a rewarding or aversive experience in the subject animal.

In other aspects the method includes where the stimulant is a physical stimulant. In some cases, physical stimulant is a foot shock.

Aspects of the present disclosure include a flow-assisted clearing device, the device comprising: a sample chamber comprising an inlet and an outlet, wherein the inlet delivers the buffer into the sample chamber and the outlet draws the buffer out of the sample chamber; a sample holder, wherein the sample holder can be removably placed inside the sample chamber, and wherein the sample holder allows the buffer to flow through; and a buffer circulator.

In other aspects the device includes where the sample holder can hold a plurality of specimens.

In other aspects the device includes where the buffer circulator is temperature controlled.

In other aspects the device includes where the buffer circulator is configured to provide unidirectional flow of the buffer into the sample chamber.

In other aspects the device includes where buffer circulator comprises a circulator inlet and a circulator outlet that is operably connected respectively to an outlet and an inlet of a sample chamber, and wherein the buffer circulator is configured to provide buffer flow entering the inlet and exiting the outlet of the sample chamber.

In other aspects the device includes where the buffer circulator further comprises a conduit operably connected to a receptacle. In some cases, the receptacle is a buffer reservoir.

In other aspects the device includes where the buffer circulator comprises a centrifugal pump, a peristaltic pump, an oscillatory pump, or a diaphragm pump.

In other aspects the device includes a buffer filter component.

In other aspects the device is not an electrophoresis chamber.

In other aspects the device includes where the device comprises a plurality of sample chambers operably connected in parallel to the buffer circulator.

DEFINITIONS

Figure 1:
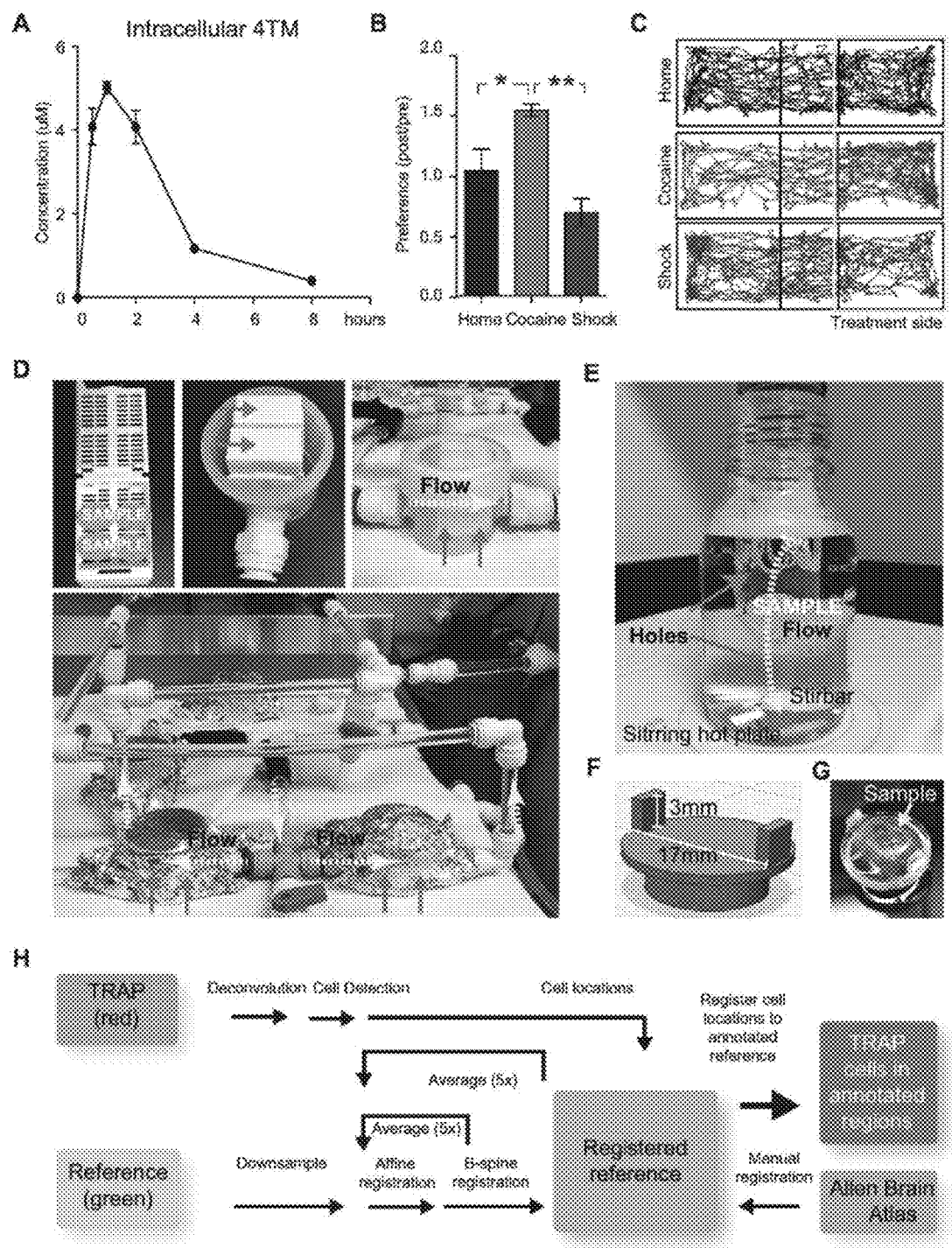
FIG. 1, panels A-M: Figures representing data showing behavioral cohort-scale brainwide activity, images showing the setup of a parallelized flow-assisted clearing device according to one embodiment, and the data processing pipeline according to one embodiment for image registration, cell detection, annotation and quantification.
Figure 1:
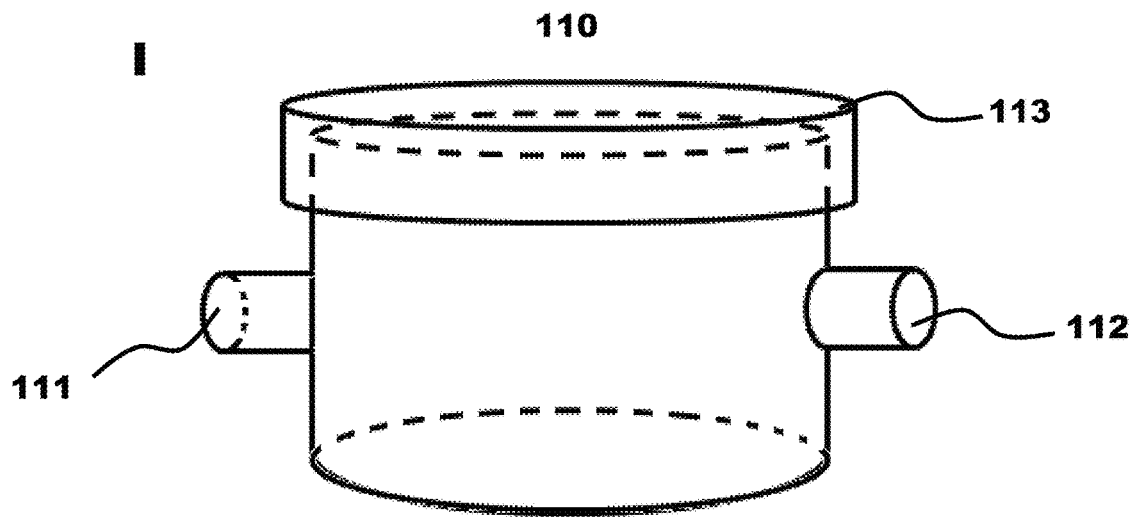
Figure 1:
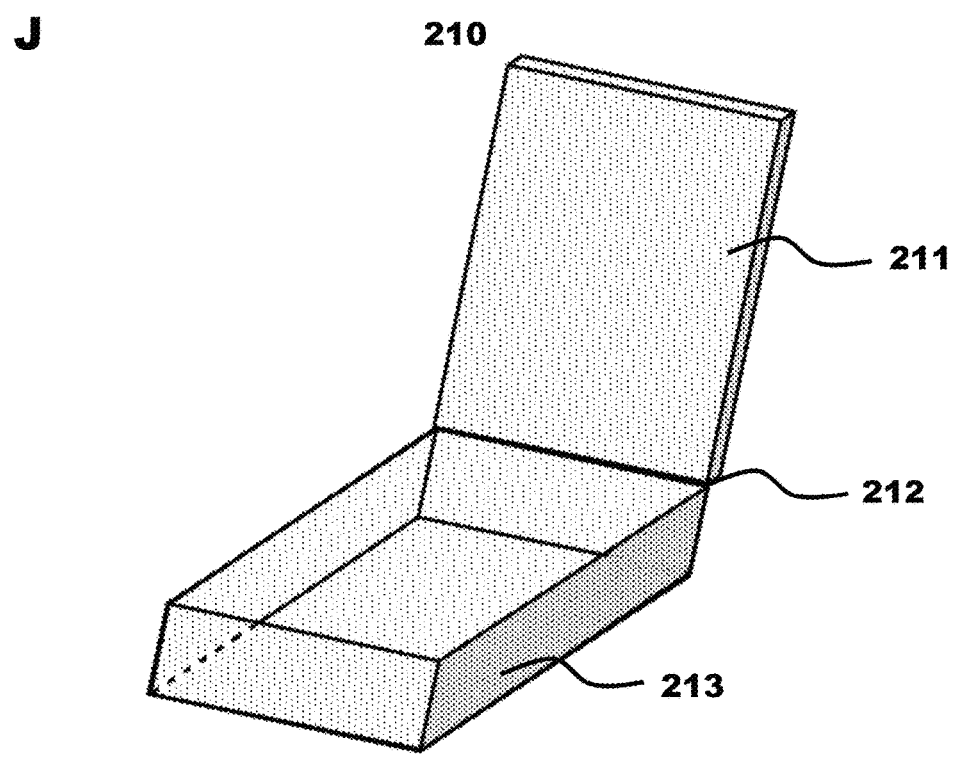
Figure 1:
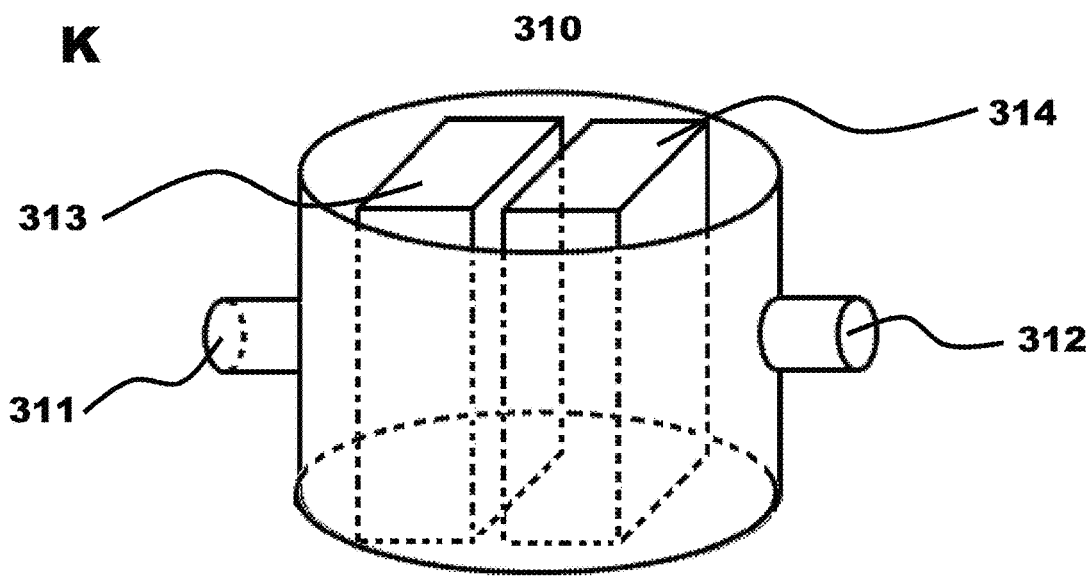
Figure 1:
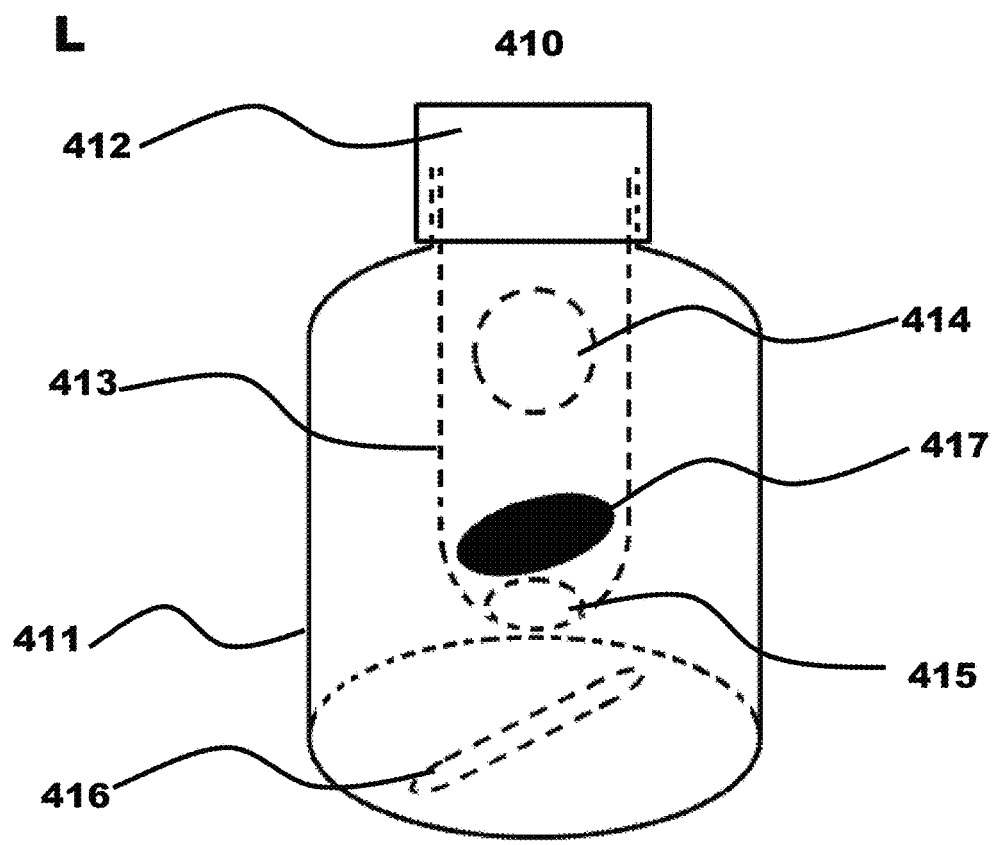
Figure 1:
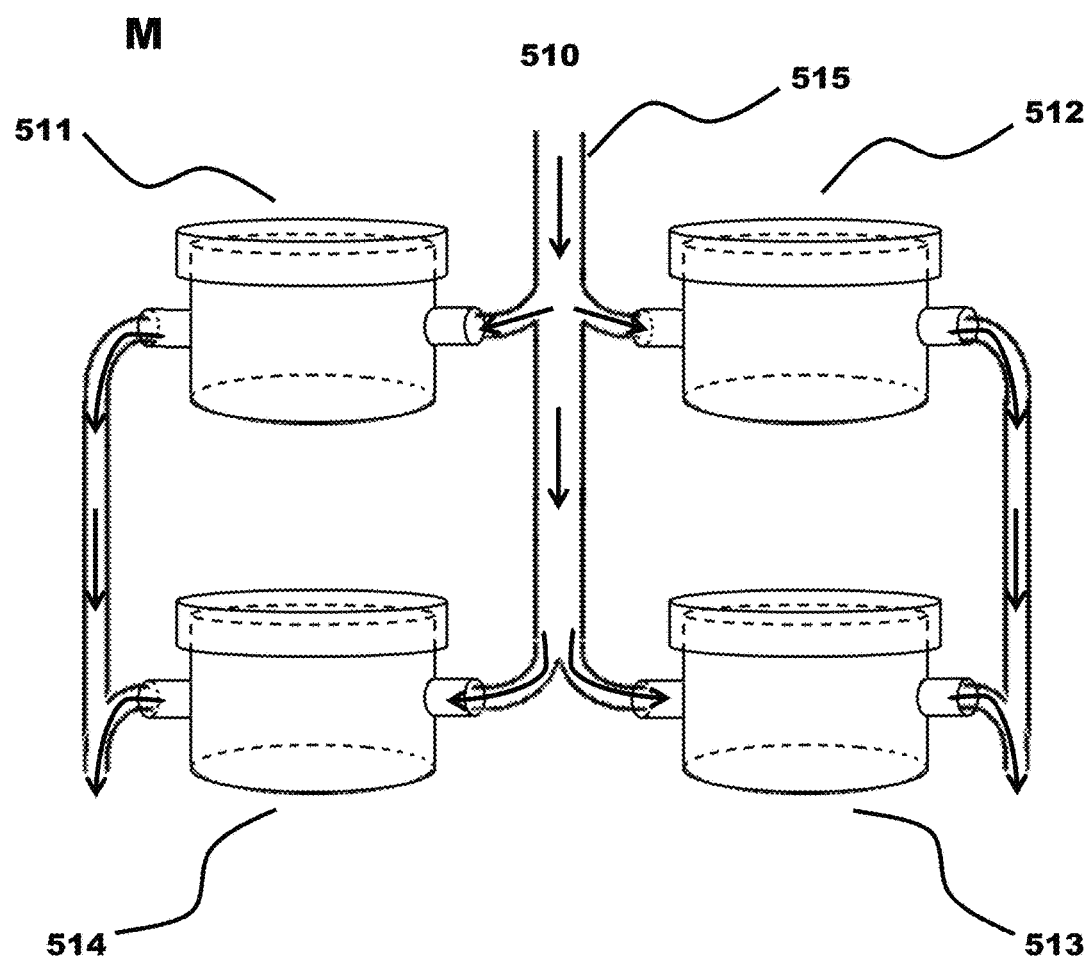

The term "biological specimen" as used herein refers to any sample of tissue or organ, or any of a variety of sample types obtained from a subject animal or a population of subject animals. The definition encompasses a whole-organ/intact organ sample, such as the brain, or a spinal cord, obtained from a subject animal. A biological specimen of the present disclosure is isolated for imaging analysis according to the methods of the present disclosure.

The term "fixing" or "fixation" as used herein encompasses the process of crosslinking cellular components of a biological specimen to each other, in order to preserve the structure of the specimen and to preserve the specimen from decay. The process of fixation includes contacting the biological specimen with a fixation agent. Various fixation agents are known in the art, and are chosen for use depending on the type of sample, and according to the purpose of fixation.

The term "hydrogel-fixed" or "hydrogel-embedded" as used herein refers to a biological specimen that has been fixed in the presence of hydrogel subunits, methods of which are further described herein. By "hydrogel" is meant a network of polymer chains that are water-insoluble, sometimes found as a colloidal gel in which water is the dispersion medium.

The term "clearing" as used herein refers to the process by which a hydrogel-embedded specimen is made substantially permeable to light. As used herein, the term "CLARITY" refers to a clearing method of preparing a biological specimen for analysis as disclosed in PCT/US2013/031066.

The term "unidirectional" as used herein refers to the single-direction flow of a buffer. For example, unidirectional flow of a buffer through a subject sample chamber comprising an inlet and an outlet, indicates that the buffer enters the chamber through the inlet, and exits the chamber through the outlet in one single direction.

The term "flow-assisted" as used herein refers the method by which a biological specimen is cleared. For example, a flow-assisted clearing device clears a biological specimen by continuous unidirectional flow of a buffer through the biological specimen.

The term "refractive index matching", e.g. as used in the term refractive index matching solution, refers to the process of immersing a subject cleared specimen in a solution to increase the resolution of a microscope when performing image capture. An refractive index matching solution has an index of refraction that closely approximates that of another object (such as a lens of a microscope).

The term "removably placed" as used herein refers to an object that can be placed and removed from a container with convenience. i.e., a removably placed object in a container is not permanently placed in the container.

The term "arranged in parallel" as used herein refers to a plurality of sample chambers of a subject clearing device arranged in a manner such that each sample chamber receives a buffer flow from the same source. Sample chambers arranged in parallel are not arranged in tandem (i.e., in series configuration), wherein the buffer entering a second sample chamber was first flowing through a first sample chamber.

The term "cellular components" generally refers to the unique, highly organized substances of which cells are composed of, e.g., membranes, organelles, proteins, nucleic acids. As used herein, cellular components, e.g., in the removal of cellular components from a biological specimen during the process of clearing, refers to the removal of lipids from the biological specimen.

The term "ionic surfactant" as used herein refers to ionic compounds that lower the surface tension between two substances.

The term "stimulant" or "stimuli" as used herein refers to a class of compounds that modulate mental or physical functions, or both. For example, stimulants may include compounds that enhance alertness, wakefulness and locomotion, or compounds that decrease mental and physical function.

The term "image volume" as used herein refers to the volume of interest in a biological specimen that is imaged by, e.g., a light-sheet microscope. The "reference image volume" refers to an image volume obtained by averaging multiple image volumes against an anatomical atlas.

The term "deconvolved" refers to the algorithm-based process used to reverse the effects of convolution on recorded data (e.g., image data).

The term "registration" generally refers to the process of transforming different sets of data into one coordinate system. For example, registration refers to the display of a plurality of images in superposition. "Linear registration" is a type of global image registration and cannot model local geometric differences between images. "Nonlinear", "elastic" or "nonrigid" image registration refer to transformations that are capable of locally warping the target image to align with a reference image.

DETAILED DESCRIPTION

The present disclosure provides methods of preparing a biological specimen for imaging analysis, comprising fixing and clearing the biological specimen and subsequently analyzing the cleared biological specimen using microscopy. Also included are methods of quantifying cells, for example, active populations of cells in response to a stimulant, and locating cells, for example, mapping the location of cells. The present disclosure also provides devices for practicing the described methods. A flow-assisted clearing device provides rapid clearing of hydrogel-embedded biological specimens without the need of specialized equipment such as electrophoresis or perfusion devices.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

The present disclosure provides methods for clearing a biological specimen and analyzing images obtained from the biological specimen. The subject methods include methods for fixing and clearing a biological specimen, as well as methods for the microscopic analysis of the biological specimen. Also provided are methods for the processing, registration, and analysis of images obtained from the microscopic analysis of the biological specimen.

Fixing

In some aspects, a biological specimen is fixed in the presence of hydrogel subunits. By "fixing" the specimen it is meant exposing the specimen, i.e., cells of the specimen, to a fixation agent such that the cellular components become crosslinked to one another. By "hydrogel" or "hydrogel network" is meant a network of polymer chains that are water-insoluble, sometimes found as a colloidal gel in which water is the dispersion medium. In other words, hydrogels are a class of polymeric materials that can absorb large amounts of water without dissolving. Hydrogels can contain over 99% water and may comprise natural or synthetic polymers, or a combination thereof. Hydrogels also possess a degree of flexibility very similar to natural tissue, due to their significant water content. A detailed description of suitable hydrogels may be found in published U.S. patent application 20100055733, herein specifically incorporated by reference. By "hydrogel subunits" or "hydrogel precursors" is meant hydrophilic monomers, prepolymers, or polymers that can be crosslinked, or "polymerized", to form a three-dimensional (3D) hydrogel network. Without being bound by any scientific theory, it is believed that this fixation of the biological specimen in the presence of hydrogel subunits crosslinks the components of the specimen to the hydrogel subunits, thereby securing molecular components in place, preserving the tissue architecture and cell morphology.

Any convenient fixation agent, or "fixative," may be used in the fixative/hydrogel composition to fix the specimen in the presence of hydrogel subunits, for example, formaldehyde, paraformaldehyde, glutaraldehyde, acetone, ethanol, methanol, etc. Typically, the fixative will be diluted in a buffer, e.g., saline, phosphate buffer (PB), phosphate buffered saline (PBS), citric acid buffer, potassium phosphate buffer, etc., usually at a concentration of about 1-10%, e.g. 1%, 2%, 3%, 4%, 5%, 6%, 7%, 8%, or 10%, for example, 4% paraformaldehyde/0.1M phosphate buffer; 2% paraformaldehyde/0.2% picric acid/0.1M phosphate buffer; 4% paraformaldehyde/0.2% periodate/1.2% lysine in 0.1 M phosphate buffer; 4% paraformaldehyde/0.05% glutaraldehyde in phosphate buffer; etc. The type of fixative used and the duration of exposure to the fixative will depend on the sensitivity of the molecules of interest in the specimen to denaturation by the fixative, and will be known by the ordinarily skilled artisan or may be readily determined using conventional histochemical or immunohistochemical techniques, for example as described in Buchwalow and Böcker. *Immunohistochemistry: Basics and Methods*. Springer-Verlag Berlin Heidelberg 2010.

The fixative/hydrogel composition may comprise any convenient hydrogel subunits, such as, but not limited to, poly(ethylene glycol) and derivatives thereof (e.g. PEG-diacrylate (PEG-DA), PEG-RGD), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose and the like. In some instances, the hydrogel subunits may be modified to add specific properties to the hydrogel; for example, peptide sequences can be incorporated to induce degradation (see, e.g., West and Hubbell, 1999, Macromolecules, 32:241) or to modify cell adhesion (see, e.g. Hem and Hubbell, 1998, J. Biomed. Mater. Res., 39:266). Agents such as hydrophilic nanoparticles, e.g., poly-lactic acid (PLA), poly-glycolic acid (PLG), poly(lactic-co-glycolic acid) (PLGA), polystyrene, poly(dimethylsiloxane) (PDMS), etc. may be used to improve the permeability of the hydrogel while maintaining patternability (see, e.g., U.S. patent application Ser. No. 13/065,030; Lee W. et al. 2010 Proc. Natl. Acad. Sci. 107, 20709-20714). Materials such as block copolymers of PEG, degradable PEO, poly(lactic acid) (PLA), and other similar materials can be used to add specific properties to the hydrogels (see, e.g., Huh and Bae, 1999, Polymer, 40:6147). Crosslinkers (e.g. bis-acrylamide, diazirine, etc.) and initiatiors (e.g. azobisisobutyronitrile (AIBN), riboflavin, L-arginine, etc.) may be included to promote covalent bonding between interacting macromolecules in later polymerization steps.

Typically, the concentration and molecular weight of the hydrogel subunit(s) and modifying agents will depend on the selected polymer and the desired characteristics, e.g., pore size, swelling properties, conductivity, elasticity/stiffness (Young's modulus), biodegradability index, etc., of the hydrogel network into which they will be polymerized. For example, it may be desirable for the hydrogel to comprise pores of sufficient size to allow the passage of macromolecules, e.g., proteins, nucleic acids, or small molecules as described in greater detail below, into the specimen. The ordinarily skilled artisan will be aware that pore size generally decreases with increasing concentration of hydrogel subunits and generally increases with an increasing ratio of hydrogel subunits to crosslinker, and will prepare a fixative/hydrogel composition that comprises a concentration of hydrogel subunits that allows the passage of such macromolecules. As another example, it may be desirable for the hydrogel to have a particular stiffness, e.g., to provide stability in handling the embedded specimen, e.g., a Young's Modulus of about 2-70 kN/m$^2$, for example, about 2 kN/m$^2$, about 4 kN/m$^2$, about 7 kN/m$^2$, about 10 kN/m$^2$, about 15 kN/m$^2$, about 20 kN/m$^2$, about 40 kN/m$^2$, but typically not more than about 70 kN/m$^2$. The ordinarily skilled artisan will be aware that the elasticity of a hydrogel network may be influenced by a variety of factors, including the branching of the polymer, the concentration of hydrogel subunits, and the degree of cross-linking, and will prepare a fixative/hydrogel composition that comprises a concentration of hydrogel subunits to provide such desired elasticity. Thus, for example, the fixative/hydrogel composition may comprise an acrylamide monomer at a concentration of from about 1% w/v to about 20% w/v, e.g., about 2% to about 15%, about 3% to about 10%, about 4% to about 8%, and a concentration of bis-acrylamide crosslinker in the range of about 0.01% to about 0.15%, e.g., 0.01%, 0.02%, 0.025%, 0.03%, 0.04%, 0.05%, 0.06%, 0.075%, 0.08%, 0.09%, 0.1% or 0.125%; or, for example, the fixative/hydrogel composition may comprise PEG prepolymers having a molecular weight ranging from at least about 2.5K to about 50K, e.g., 2.5K or more, 3.5K or more, 5K or more, 7.5K or more, 10K or more, 15K or more, 20K or more, but typically not more than about 50K, at a concentration in a range from about 1% w/w to about 50% w/w, e.g., 1% or more, 5% or more, 7.5% or more, 10% or more, 15% or more, 20% or more, 30% or more, 40% or more, and usually not more than about 50%. Concentrations of hydrogel subunits and modifiers that provide desired hydrogel characteristics may be readily determined by methods in the art or as described in the working examples below.

The fixative/hydrogel solution may be delivered to the specimen by any convenient method, e.g., perfusion, injection, instillation, absorption, application, immersion/submersion, etc. In certain aspects, the subject method delivers the hydrogel solution to the specimen using a non-perfusion-based method. The specimen will typically be fixed in the presence of the hydrogel for 15 minutes or more, for example, for 30 minutes or more, 1 hour or more, 2 hours or more, 4 hours or more, 6 hours or more, 12 hours or more, in some instances, for 16 hours or more, 20 hours or more, 24 hours or more, or 48 hours or more.

Following fixation of the specimen, the hydrogel subunits are polymerized, i.e., covalently or physically crosslinked, to form a hydrogel network. Polymerization may be induced by any method including, but not limited to, thermal cross-linking, chemical crosslinking, physical crosslinking, ionic crosslinking, photo-crosslinking, irradiative crosslinking (e.g., x-ray, electron beam), and the like, and may be selected based on the type of hydrogel used and knowledge in the art. For example, mixing of an un-polymerized or partially polymerized resin with specific crosslinking chemicals results in a chemical reaction that forms cross-links. As another example, polymerization can be induced by the addition of a non-nitrile azo thermal initiator, such as VA-044, which is inert at lower temperatures, but generates free radicals in solution at higher temperatures. The free radicals that are generated initiate polymerization of the acrylamide monomers to form a crosslinked hydrogel network. Concentrations of crosslinking agents and thermal initiators may be readily determined by methods in the art or as described in the working examples below. Crosslinking can be induced in materials that are normally thermoplastic through exposure to a radiation source, such as electron beam exposure, gamma-radiation, or UV light; for example, electron beam processing is used to polymerize the C type of crosslinked polyethylene. Other types of crosslinked polyethylene are made by addition of peroxide during extruding (type A) or by addition of a cross-linking agent (e.g. vinylsilane) and a catalyst during extruding and then performing a post-extrusion curing. Many polymers undergo oxidative cross-linking, typically when exposed to atmospheric oxygen. In some cases the reaction is more rapid than desired and thus polymerization reactions may involve the use of an antioxidant to slow the formation of oxidative cross-links. In other cases, e.g., when more rapid formation of cross-links by oxidation is desirable, an oxidizer such as hydrogen peroxide may be used to speed up the process. The length of time for polymerization will depend on the type of hydrogel subunits used and the chosen polymerization method, but will typically be about 15 minutes to about 48 hours, for example, 15 minutes or more, 1 hour or more, 2 hours or more, 3 hours or more, 4 hours or more, 6 hours or more, 12 hours or more, 16 hours or more, 24 hours or more, or in some instances, 48 hours. The optimal time and combination of reagents will be known to the ordinarily skilled artisan or may be determined empirically or from any number of publicly available resources (e.g., on the world wide web at piercenet.com; see also, Macroporous Polymers: Production Properties and Biotechnological/Biomedical Applications. Edited by Bo Mattiasson, Ashok Kumar, and Igor Yu. Galeaev. CRC Press 2010; and Crosslinking Reagents Technical Handbook, Pierce Biotechnology, Inc., 2006).

Clearing

Once polymerized, the hydrogel-embedded (i.e., hydrogel-hybridized) specimen may be cleared. By "clearing" a specimen it is meant that the specimen is made substantially permeable to light, i.e., transparent. In other words, about 70% or more of the visual (i.e., white) light, ultraviolet light or infrared light that is used to illuminate the specimen will to pass through the specimen and illuminate only selected cellular components therein, e.g., 75% or more of the light, 80% or more of the light, 85% or more of the light, in some instances, 90% or more of the light, 95% or more of the light, light, 98% or more of the light, e.g. 100% of the light will pass through the specimen. This change in the optical properties of the specimen provides for the visualization of cellular and subcellular structures internal to the tissue.

Any treatment that forces cellular components, e.g., lipids, from the specimen, that draws cellular components, e.g., lipids, from a specimen, or that causes cellular components, e.g., lipids, to break down, i.e., dissolve, within a specimen may be used to clear the specimen, including, without limitation, exposure to organic solvents such as xylenes, ethanol or methanol, exposure to detergents such as saponin, Triton X-100 and Tween-20, exposure to ionic surfactants, e.g., sodium dodecyl sulfate (SDS), electrophoresis, hydrodynamic pressure, ultrasonic vibration, solute contrasts, microwave radiation, vascular circulation, and the like. In some instances, clearing is performed using a solvent that does not quench fluorescent proteins. Examples of organic solvents that are known to quench fluorescent proteins include tetrahydrofuran, hexane, benzylalcohol/benzylbenzoate (BABB), and dibenzyl ether. Accordingly, in order to preserve the fluorescence of various proteins, in some embodiments clearing is conducted using solvents other than those listed above, e.g., is conducted using non-organic solvents.

In some instances, clearing is conducted using an ionic surfactant, e.g., SDS, in order to expedite the clearing process by actively transporting charged ionic micelles out of the specimen that is being cleared. Clearing may be performed in any convenient buffer that is compatible with the selected clearance method, e.g., saline, phosphate buffer, phosphate buffered saline (PBS), sodium borate buffer, boric acid buffer, citric acid buffer, etc., as known in the art, and will typically take about 1-10 days per centimeter thickness of specimen, i.e., usually about 1 day, in some instances 2 days, sometimes 5 days, and typically no more than 10 days per cubic centimeter. Optimal time may be readily determined by visual inspection of the specimen for clarity.

After clearing, a sample will generally be substantially free of lipids. By "substantially free of lipids" is meant that the original amount of lipids present in the sample before clearing has been reduced by approximately 70% or more, such as by 75% or more, such as by 80% or more, such as by 85% or more, such as by 90% or more, such as by 95% or more, such as by 99% or more, such as by 100%.

Post-Clearing

In some instances, no further manipulation of the specimen will be necessary for microscopic analysis. For example, the specimen may comprise biomolecules that can be directly visualized by microscopy. By "biomolecules" it is generally meant proteins, lipids, steroids, nucleic acids, etc. within a tissue or cell. One example of this would be if the organism that was the source of the specimen expressed a protein that possesses the ability to fluoresce, i.e. a "fluorescent protein", or "FP". By "fluoresce" is meant to absorb energy at one wavelength and emit it at another wavelength. For example, a green fluorescent protein (GFP) refers to a polypeptide that has a peak in the emission spectrum at 510 nm or about 510 nm. A variety of FPs that emit at various wavelengths are known in the art. FPs of interest include, but are not limited to, a green fluorescent protein (GFP), yellow fluorescent protein (YFP), orange fluorescent protein (OFP), cyan fluorescent protein (CFP), blue fluorescent protein (BFP), red fluorescent protein (RFP), far-red fluorescent protein, or near-infrared fluorescent protein. As used herein, *Aequorea* GFP refers to GFPs from the genus *Aequorea* and to mutants or variants thereof. Such variants and GFPs from other species, such as *Anthozoa* reef coral, *Anemonia* sea anemone, *Renilla* sea pansy, *Galaxea* coral, *Acropora* brown coral, *Trachyphyllia* and *Pectimidae* stony coral and other species are well known and are available and known to those of skill in the art. Exemplary GFP variants include, but are not limited to BFP, CFP, YFP and OFP. Examples of florescent proteins and their variants include GFP proteins, such as Emerald (Invitrogen, Carlsbad, Calif.), EGFP (Clontech, Palo Alto, Calif.), Azami-Green (MBL International, Woburn, Mass.), Kaede (MBL International, Woburn, Mass.), ZsGreenl (Clontech, Palo Alto, Calif.) and CopGFP (Evrogen/Axxora, LLC, San Diego, Calif.); CFP proteins, such as Cerulean (Rizzo, Nat Biotechnol. 22(4):445-9 (2004)), mCFP (Wang et al., PNAS USA. 101(48):16745-9 (2004)), AmCyanl (Clontech, Palo Alto, Calif.), MiCy (MBL International, Woburn, Mass.), and CyPet (Nguyen and Daugherty, Nat Biotechnol. 23(3): 355-60 (2005)); BFP proteins such as EBFP (Clontech, Palo Alto, Calif.); YFP proteins such as EYFP (Clontech, Palo Alto, Calif.), YPet (Nguyen and Daugherty, Nat Biotechnol. 23(3):355-60 (2005)), Venus (Nagai et al., Nat. Biotechnol. 20(1):87-90 (2002)), ZsYellow (Clontech, Palo Alto, Calif.), and mCitrine (Wang et al., PNAS USA. 101(48):16745-9 (2004)); OFP proteins such as cOFP (Strategene, La Jolla, Calif.), mKO (MBL International, Woburn, Mass.), and mOrange; and others (Shaner N C, Steinbach P A, and Tsien R Y., Nat Methods. 2(12):905-9 (2005)). Another class of fluorescent proteins is the red fluorescent protein Discosoma RFP (DsRed) that has been isolated from the corallimorph Discosoma (Matz et al., Nature Biotechnology 17: 969-973 (1999)), and red or far-red fluorescent proteins from any other species, such as *Heteractis* reef coral and *Actinia* or *Entacmaea* sea anemone, as well as variants thereof RFPs include, for example, Discosoma variants, such as monomeric red fluorescent protein 1 (mRFP1), mCherry, tdTomato, mStrawberry, mTangerine (Wang et al., PNAS USA. 101(48):16745-9 (2004)), DsRed2 (Clontech, Palo Alto, Calif.), and DsRed-T1 (Bevis and Glick, Nat. Biotechnol., 20: 83-87 (2002)), Anthomedusa J-Red (Evrogen) and *Anemonia* AsRed2 (Clontech, Palo Alto, Calif.). Far-red fluorescent proteins include, for example, *Actinia* AQ143 (Shkrob et al., Biochem J. 392(Pt 3):649-54 (2005)), *Entacmaea* eqFP611 (Wiedenmann et al. Proc Natl Acad Sci USA. 99(18):11646-51 (2002)), Discosoma variants such as mPlum and mRasberry (Wang et al., PNAS USA. 101(48): 16745-9 (2004)), and *Heteractis* HcRed1 and t-HcRed (Clontech, Palo Alto, Calif.).

Additionally or alternatively, it may be desirable to contact the cells and intracellular structures of the specimen with one or more macromolecules prior to microscopic analysis. For example, macromolecules may be provided that promote the visualization of particular cellular biomolecules, e.g., proteins, lipids, steroids, nucleic acids, etc. and sub-cellular structures. In some embodiments, the macromolecules are diagnostic. In some embodiments, the macromolecules are prognostic. In some embodiments, the macromolecules are predictive of responsiveness to a therapy. In some embodiments, the macromolecules are candidate agents in a screen, e.g., a screen for agents that will aid in the diagnosis and/or prognosis of disease, in the treatment of a disease, and the like.

For example, specimens may be contacted with nucleic acid stains like DAPI and Hoechst, which bind the minor groove of DNA, thus labeling the nuclei of cells. Drugs or toxins that bind specific cellular structures and have been derivatized with a fluorescent reporter may be employed, e.g., fluorescently labelled-phalloidin, which is used to stain actin fibers in mammalian cells. There are many fluorescent reported molecules, called fluorophores or fluorochromes such as fluorescein, Alexa Fluors or DyLight 488, which can be chemically linked to molecules which bind the target biomolecules of interest within the sample.

As another example, the specimen may be contacted with one or more polypeptides, e.g. antibodies, labeled peptides, and the like, that are specific for and will bind to particular cellular biomolecules for either direct or indirect labeling by color or immunofluorescence. By immunofluorescence it is meant a technique that uses the highly specific binding of an antibody to its antigen or binding partner in order to label specific proteins or other molecules within the cell. A sample is treated with a primary antibody specific for the biomolecule of interest. A fluorophore can be directly conjugated to the primary antibody or peptide. Alternatively a secondary antibody, conjugated to a detection moiety or fluorophore, which binds specifically to the first antibody can be used. See, for example, Buchwalow and Bocker. Immunohistochemistry: Basics and Methods, Springer-Verlag, Berlin Heidelberg 2010, and Hayat, M. A. Microscopy, Immunohistochemistry, and Antigen Retrieval Methods for Light and Electron Microscopy. Kluwar Academic Publishers, New York 2002, for examples of protocols that may be followed. Peptides that are specific for a target cellular biomolecule and that are conjugated to a fluorophor or other detection moiety may also be employed.

Another example of a class of agents that may be provided as macromolecules is nucleic acids. For example, a specimen may be contacted with an antisense RNA that is complementary to and specifically hybridizes to a transcript of a gene of interest, e.g., to study gene expression in cells of the specimen. As another example, a specimen may be contacted with a DNA that is complementary to and specifically hybridizes to genomic material of interest, e.g., to study genetic mutations, e.g., loss of heterozygosity, gene duplication, chromosomal inversions, and the like. The hybridizing RNA or DNA is conjugated to detection moieties, i.e. agents that may be either directly or indirectly visualized microscopically. Examples of in situ hybridization techniques may be found at, for example, Harris and Wilkinson. In situ hybridization: Application to developmental biology and medicine, Cambridge University Press 1990; and Fluorescence In Situ Hybridization (FISH) Application Guide. Liehr, T, ed., Springer-Verlag, Berlin Heidelberg 1990.

As another example, the specimen may be contacted with small molecules. For example, if the specimen comprises β-galactosidase or alkaline phosphatase, it may be desirable to visualize cells and regions of the tissue expressing these proteins. Towards this end, a specimen may be contacted with substrates for β-galactosidase (e.g. X-gal, 4-Trifluoromethylumbelliferyl-β-D-galactopyranoside (TFMU-Gal), Resoruf in β-D-galactopyranoside (Res-gal), 4-Methylumbelliferyl β-D-galactopyranoside (MUG), di-β-D-galactopyranoside (FDG), Carboxyumbelliferyl β-D-galactopyranoside (CUG)) or for alkaline phosphatase (e.g. nitro-blue tetrazolium (NBT)/5-bromo-4-chloro-3'-indolyphosphate (BCIP)) and other reagents that allow for visualization of β-galactosidase or alkaline phosphatase activity. As another example, it may be desirous to visualize the dendritic arbors and spins of neurons in, e.g., a CNS specimen. To do so, the specimen may be exposed to chemicals used in Golgi-Cox impregnation, e.g., 3% potassium bichromate followed by a 2% silver nitrate solution.

In some instances, the biomolecules that are targeted by the provided macromolecules are endogenous to the cell. In other instances, the macromolecules may be provided to the specimen to target/visualize biomolecules that were ectopically provided to the cells of the specimen, e.g. agents that were introduced to the specimen in vivo or ex vivo to label certain cell populations or subcellular structures. For example, stereotactic surgery is often used in the field of neuroscience to provide biomolecules such as proteins, viruses, chemicals to neural tissue that label, or "trace", the projections and/or the connectivity of subsets of neurons in vivo or ex vivo. In this technique, a needle comprising a labeling macromolecule is lowered into CNS tissue at a precise location and the labeling molecule is released into the tissue. The molecule will fill the neurons in the vicinity of the injection site and, depending on the type of macromolecule delivered, may be transported across synapses to label their efferent targets ("anterograde tracing") and/or across dendrites to label the afferent neurons from which they are receiving signals ("retrograde tracing"). Examples of agents that may be used to label neurons stereotactically are well known in the art, including, for example, nucleic acids that encode fluorescent proteins; viral tracers, e.g. Herpes simplex virus type1 (HSV) and the Rhabdoviruses; wheat-germ agglutinin (WGA); *Phaseolus vulgaris* leucoagglutinin (PHA-L); horseradish peroxidase-conjugated lectins; biotinylated dextran amines (BDA); cholera toxin B; NEUROBIOTIN Tracer® (Vector labs). Specimens labeled in this way may be contacted with macromolecules, e.g. polypeptides or chemicals, that promote the visualization of these ectopically provided labels.

In some instances, the macromolecules that are used to visualize the cellular biomolecules or subcellular structures are passively transported into the specimen. In other words, the macromolecules diffuse into the specimen. In other instances, the macromolecules are actively transported into the specimen, e.g. by electroporation, hydrodynamic pressure, ultrasonic vibration, solute contrasts, microwave radiation, vascular circulation, or the like. In some embodiments, the specimen is contacted with the macromolecules after the specimen has been cleared. In other embodiments, the hydrogel-embedded specimen may be contacted with the macromolecules prior to clearing the specimen. In such embodiments, contact with the macromolecules may be facilitated by permeabilizing the specimen, that is, changing the properties of the specimen to improve the permeability of the specimen to macromolecules. By a "permeabilized" specimen it is meant that about 50% or more of the macromolecules applied to the specimen will penetrate to the deepest regions of the specimen, e.g. 60% or more of the macromolecules, 70% or more of the macromolecules, or 80% or more of the macromolecules, in some instances 85% or more of the macromolecules, 90% or more of the macromolecules, or 95% or more of the macromolecules, for example 98% or more of the macromolecules, e.g. 100% of the macromolecules will pass through the specimen. Permeabilization of the specimen, and of the cells therein, may be achieved by any of the protocols discussed above for the removal of cellular components, e.g. lipids, from the specimen or as known in the art for permeabilizing cells.

In some instances, a technique called Targeted Recombination in Active Populations (TRAP) may be employed to identify a certain active population of cells within a specimen. In some aspects, TRAP is used to identify a neuronal population within a specimen that is activated by experiences. In some cases, an activated neuronal population may be identified by genetically engineering a subject animal to obtain permanent or temporary genetic access to the activated neuronal population. TRAP utilizes two genetic components: a transgene that takes advantage of immediate early gene (IEG) regulatory elements to express a drug-dependent recombinase (e.g., tamoxifen-dependent Cre recombinase CreER$^{T2}$), in an activity-dependent manner, and a transgene or virus that expresses an effector protein in a recombination-dependent manner. IEGs are genes which are activated transiently and rapidly in response to a wide variety of defined stimuli, and represent a standing response mechanism that is activated at the transcription level in the first round of response to the defined stimuli. TRAP may utilize any endogenous IEG loci of the subject animal, including, but not limited to: Fos, Arc and jun, to express a drug-dependent recombinase (e.g., tamoxifen-dependent Cre recombinase CreER$^{T2}$). TRAP can selectively provide access to neurons activated by, but not limited to, specific somatosensory, visual, and auditory stimuli, and by experience in a novel environment. See, e.g., Guenthner et al., Neuron (2013) 78(5):773-784.

Suitable Specimens

Tissue specimens suitable for use with the methods and systems described herein generally include any type of tissue specimens collected from living or dead subjects, such as, e.g., biopsy specimens and autopsy specimens. Tissue specimens may be collected and processed using the methods and systems described herein and subjected to microscopic analysis immediately following processing, or may be preserved and subjected to microscopic analysis at a future time, e.g., after storage for an extended period of time. In some embodiments, the methods described herein may be used to preserve tissue specimens in a stable, accessible and fully intact form for future analysis. For example, tissue specimens, such as, e.g., human brain tissue specimens, may be processed as described above and cleared to remove a plurality of cellular components, such as, e.g., lipids, and then stored for future analysis. In some embodiments, the methods and systems described herein may be used to analyze a previously-preserved or stored tissue specimen. For example, in some embodiments a previously-preserved tissue specimen that has not been subjected to the CLARITY process may be processed and analyzed as described herein.

Microscopic Analysis

To microscopically visualize specimens prepared by the subject methods, in some embodiments the specimen is embedded in a mounting medium. Mounting medium is typically selected based on its suitability for the reagents used to visualize the cellular biomolecules, the refractive index of the specimen, and the microscopic analysis to be performed. For example, for phase-contrast work, the refractive index of the mounting medium should be different from the refractive index of the specimen, whereas for bright-field work the refractive indexes should be similar. As another example, for epifluorescence work, a mounting medium should be selected that reduces fading, photobleaching or quenching during microscopy or storage. In certain embodiments, a mounting medium or mounting solution may be selected to enhance or increase the optical clarity of the cleared tissue specimen. Nonlimiting examples of suitable mounting media that may be used include glycerol, CC/Mount™, Fluoromount™ Fluoroshield™, ImmunHistoMount™, Vectashield™, Permount™, Acrytol™, CureMount™, FocusClear™, RapidClear™, or equivalents thereof.

In some instances, the hydrogel-embedded specimen is permanently mounted. In other words, once mounted in mounting medium, the hydrogel-embedded specimen cannot be removed for further manipulation. In other instances, the specimen is temporarily, or reversibly, mounted. In other words, the hydrogel-embedded specimen may be removed from the mounting medium and re-stained after microscopy to visualize alternative/additional biomolecules or subcellular structures. In such instances, macromolecules that were previously added to the specimen, e.g. to visualize certain biomolecules, may be removed after microscopic analysis by, e.g., exposure to organic solvents such as xylenes, ethanol or methanol, exposure to detergents such as sodium dodecyl sulfate (SDS), saponin, Triton X-100 and Tween-20, electrophoresis, hydrodynamic pressure, ultrasonic vibration, solute contrasts, microwave radiation, vascular circulation, and the like. The hydrogel-embedded specimen is then contacted with different macromolecules specific for other biomolecules or subcellular structures. As such, iterative staining may be performed on the same specimen.

Specimens prepared using the subject methods may be analyzed by any of a number of different types of microscopy, for example, optical microscopy (e.g. bright field, oblique illumination, dark field, phase contrast, differential interference contrast, interference reflection, epifluorescence, confocal, etc., microscopy), laser microscopy, electron microscopy, and scanning probe microscopy.

Bright field microscopy is the simplest of all the optical microscopy techniques. Sample illumination is via transmitted white light, i.e. illuminated from below and observed from above. Limitations include low contrast of most biological samples and low apparent resolution due to the blur of out of focus material. The simplicity of the technique and the minimal sample preparation required are significant advantages.

In oblique illumination microscopy, the specimen is illuminated from the side. This gives the image a 3-dimensional appearance and can highlight otherwise invisible features. A more recent technique based on this method is Hoffmann's modulation contrast, a system found on inverted microscopes for use in cell culture. Though oblique illumination suffers from the same limitations as bright field microscopy (low contrast of many biological samples; low apparent resolution due to out of focus objects), it may highlight otherwise invisible structures.

Dark field microscopy is a technique for improving the contrast of unstained, transparent specimens. Dark field illumination uses a carefully aligned light source to minimize the quantity of directly-transmitted (unscattered) light entering the image plane, collecting only the light scattered by the sample. Dark field can dramatically improve image contrast (especially of transparent objects) while requiring little equipment setup or sample preparation. However, the technique suffers from low light intensity in final image of many biological samples, and continues to be affected by low apparent resolution.

Phase contrast is an optical microscopy illumination technique that converts phase shifts in light passing through a transparent specimen to brightness changes in the image. In other words, phase contrast shows differences in refractive index as difference in contrast. The phase shifts themselves are invisible to the human eye, but become visible when they are shown as brightness changes.

In differential interference contrast (DIC) microscopy, differences in optical density will show up as differences in relief. The system consists of a special prism (Nomarski prism, Wollaston prism) in the condenser that splits light in an ordinary and an extraordinary beam. The spatial difference between the two beams is minimal (less than the maximum resolution of the objective). After passage through the specimen, the beams are reunited by a similar prism in the objective. In a homogeneous specimen, there is no difference between the two beams, and no contrast is being generated. However, near a refractive boundary (e.g. a nucleus within the cytoplasm), the difference between the ordinary and the extraordinary beam will generate a relief in the image. Differential interference contrast requires a polarized light source to function; two polarizing filters have to be fitted in the light path, one below the condenser (the polarizer), and the other above the objective (the analyzer).

Another microscopic technique using interference is interference reflection microscopy (also known as reflected interference contrast, or RIC). It is used to examine the adhesion of cells to a glass surface, using polarized light of a narrow range of wavelengths to be reflected whenever there is an interface between two substances with different refractive indices. Whenever a cell is attached to the glass surface, reflected light from the glass and that from the attached cell will interfere. If there is no cell attached to the glass, there will be no interference.

A fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" refers to any microscope that uses fluorescence to generate an image, whether it is a more simple set up like an epifluorescence microscope, or a more complicated design such as a confocal microscope, which uses optical sectioning to get better resolution of the fluorescent image.

Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (i.e., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples.

In single plane illumination microscopy (SPIM), also known as light sheet microscopy, only the fluorophores in the focal plane of the detection objective lens are illuminated. The light sheet is a beam that is collimated in one and focused in the other direction. Since no fluorophores are excited outside the detectors' focal plane, the method also provides intrinsic optical sectioning. Moreover, when compared to conventional microscopy, light sheet methods exhibit reduced photobleaching and lower phototoxicity, and often enable far more scans per specimen. By rotating the specimen, the technique can image virtually any plane with multiple views obtained from different angles. In some cases, a specimen cleared by methods of the present disclosure may be imaged with high resolution by illuminating the cleared specimen with two light sheets from a first side and a second side to produce an image volume.

Super-resolution microscopy is a form of light microscopy. Due to the diffraction of light, the resolution of conventional light microscopy is limited as stated by Ernst Abbe in 1873. A good approximation of the resolution attainable is the FWHM (full width at half-maximum) of the point spread function, and a precise widefield microscope with high numerical aperture and visible light usually reaches a resolution of ~250 nm. Super-resolution techniques allow the capture of images with a higher resolution than the diffraction limit. They fall into two broad categories, "true" super-resolution techniques, which capture information contained in evanescent waves, and "functional" super-resolution techniques, which use experimental techniques and known limitations on the matter being imaged to reconstruct a super-resolution image.

Laser microscopy uses laser illumination sources in various forms of microscopy. For instance, laser microscopy focused on biological applications uses ultrashort pulse lasers, or femtosecond lasers, in a number of techniques including nonlinear microscopy, saturation microscopy, and multiphoton fluorescence microscopy such as two-photon excitation microscopy (a fluorescence imaging technique that allows imaging of living tissue up to a very high depth, e.g. one millimeter)

In electron microscopy (EM), a beam of electrons is used to illuminate a specimen and produce a magnified image. An electron microscope has greater resolving power than a light-powered optical microscope because electrons have wavelengths about 100,000 times shorter than visible light (photons). They can achieve better than 50 pm resolution and magnifications of up to about 10,000,000× whereas ordinary, non-confocal light microscopes are limited by diffraction to about 200 nm resolution and useful magnifications below 2000×. The electron microscope uses electrostatic and electromagnetic "lenses" to control the electron beam and focus it to form an image. These lenses are analogous to but different from the glass lenses of an optical microscope that form a magnified image by focusing light on or through the specimen. Electron microscopes are used to observe a wide range of biological and inorganic specimens including microorganisms, cells, large molecules, biopsy samples, metals, and crystals. Industrially, the electron microscope is often used for quality control and failure analysis. Examples of electron microscopy include Transmission electron microscopy (TEM), Scanning electron microscopy (SEM), reflection electron microscopy (REM), Scanning transmission electron microscopy (STEM) and low-voltage electron microscopy (LVEM).

Scanning probe microscopy (SPM) is a branch of microscopy that forms images of surfaces using a physical probe that scans the specimen. An image of the surface is obtained by mechanically moving the probe in a raster scan of the specimen, line by line, and recording the probe-surface interaction as a function of position. Examples of SPM include atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM).

Image Processing

Provided are image processing methods for the visualization and analysis of a biological specimen that has been imaged using light-sheet imaging. In certain aspects, the biological specimen being imaged has been processed (e.g., cleared) by a device of the present disclosure. In some cases, the biological specimen being imaged has been cleared by a flow-assisted device of the present disclosure.

In certain aspects, raw images of the cleared biological specimen can be acquired on a light sheet fluorescence microscope and stored in a compressed or uncompressed format. Suitable raw image file formats include but are not limited to, e.g., BMP, BPG, GIF, HDR, JPEG 2000, JPEG XR, JPEG/JFIF, Layered Image File Format, HEIF, ILBM, ILBM, IMG, Nrrd, PAM, PBM, PCX, PGF, PGM, PLBM, PNG, PNM, TIFF, VICAR, WEBP, PPM, SGI, SID, Sun Raster, TGA, CD5, DEEP, ECW, Exif, FITS, FLIF, and the like. Raw images obtained from the light sheet fluorescence microscope may be of a variety of image bit depth depending on the type of image captures and the sensitivity of the image acquiring device. Raw image bit depth may include but are not limited to, e.g., 8-bit, 10-bit, 12-bit, 14-bit, 16-bit, 18-bit, 24-bit, 30-bit, 36-bit, 48-bit, 64-bit, and the like. For example, raw images may be acquired as 16-bit TIFF files.

In some aspects, raw images may be further processed by three dimensional (3D) deconvolution. "Deconvolution" as used herein, generally refers to the process of reversing the optical distortion that takes place in an imaging instrument (e.g., light-sheet fluorescence microscope) to create sharper images. In some cases, 3D deconvolution of the raw images may comprise the use of a point spread function (PSF), a function that describes the distortion of the image in terms of the pathway a theoretical point source of light takes through the imaging instrument. In some cases, the PSF can be determined and an inverse or complementary function is computed to convolve the raw image, resulting in the original, undistorted image. In other cases, the PSF cannot be completely determined, and an approximation of the PSF may be used instead. When the PSF is unknown, the PSF may be deduced by systematically testing different possible PSFs and assessing whether the raw image becomes improved, a procedure known as blind deconvolution. In some cases, raw images may be further processed by blind deconvolution that employ algorithms such as but not limited to, e.g., Richardson-Lucy deconvolution algorithm, the Wiener deconvolution, and the like. 3D deconvolution of raw images can be achieved using commercial software (e.g., AutoQuantX3). Depending on the method used, different parameters may be defined, including but not limited to, e.g., modality, iterations, noise, montage, overlap, NA, spacing, magnitude and the like. A person of skill in the art will be able to determine the proper settings for various parameters depending on the method being used and depending on the application, and depending on the actual experiment being carried out.

In some aspects, after the raw images have been deconvolved, the deconvolved images may be 3D-rendered and visualized for taking snapshot images and making movies. The process of 3D rendering generally comprises automatically converting 3D wire frame models into 2D images with 3D photorealistic effects of non-photorealistic rendering on a computer. Various 3D rendering methods available in the art may be used, including but not limited to, e.g., real-time rendering, non real-time rendering, non real-time photorealistic rendering (e.g., ray tracing, radiosity, and the like), and the like. 3D-rendering of deconvolved images can be achieved using commercially available software (e.g., Imaris). A person of skill in the art will be able to determine the proper settings for various parameters depending on the method being used for 3D rendering of the deconvolved images.

Image Registration

After deconvolution, the raw images of the biological specimens may be used to generate an average reference. In certain aspects, an average reference may be generated by steps comprising: globally aligning sample specimen images to an atlas (e.g., Allen Brain Atlas), affine registering each sample specimen to the current average reference five times, averaging the resulting registered sample specimens to provide input to the next iteration of the average reference. The above steps may be repeated for multiple iterations to obtain an average reference. See, examples section below for detailed procedures on one embodiment of how an average reference is generated.

Any of the known matching and registration processes may be used, for instance based on detection and comparison of intensities, or intensity distributions, or detection and comparison of edges or of geometric structures. For example, affine registration is a linear mapping method that preserves points, straight lines, and planes, typically used to correct for geometric distortions or deformations that occur. Other matching techniques which may be used are described, for example in "Accurate Three-Dimensional Registration of CT, PET and/or MR Images of the Brain", by Pelizzari, C. A., et al., Journal of Computer Assisted Tomography, Volume 13, 1989; "MRI-PET Registration with Automated Algorithm" by Woods, R. P., et al., Journal of Computer Assisted Tomography, Volume 17, 1993; "The Principle Axis Transformation—A Method for *Image Registration*", by Albert, N. M., et al., Journal of Nuclear Medicine, Volume 31, 1990; "New Feature Points Based on Geometrical Invariance for 3-D *Image Registration*", Research Report Number 2149 from the INRIA, Jean-Philippe Thirion; and "A survey of medical *Image Registration*", by J. B. Antoine Maintz, M. Viergever, Medical Image Analysis, 2(1): 1 36, 1998, all of which are herein incorporated by reference.

Cell Quantification or Location

The present disclosure provides methods for the quantification of cells or locating cells in a raw image (e.g., sample specimen image). In some aspects, the quantification or locating of cells is directed to the quantification of active populations of cells, e.g. the quantification of TRAP labeled cells. In other aspects, the quantification or locating of cells is directed to any labeled cell in the specimen. In a certain aspect, quantification of cells may comprise: nonlinearly registering sample specimen images to the average reference, generating binary mask volumes for each region of the specimen in the atlas, and computing the number of warmed cell locations in each region. In some cases, generating a binary mask volume for each region in the atlas can be performed by manually drawing the regions, or can be performed from an aligned atlas. In some cases, regions known to have strong non-specific labeling may be excluded from analysis. See examples section for detailed description of cell quantification of ArcTRAP labeled brains.

Cohort-Scale Analysis

Methods provided by the present disclosure may allow for a cohort-scale analysis of biological specimens. For example, methods provided may allow for a cohort-scale analysis of behavior. In some aspects, devices and systems of the present disclosure (e.g., a parallelized flow-assisted clearing device) allow for the rapid processing and clearing of multiple biological specimens (e.g., obtained from a cohort of subject animals). Coupled with labeling methods described herein, analysis of biological specimens in a cohort of animals may be achieved. For example, the examples section describes the cohort-scale analysis of mouse brains after the mice have been stimulated with a stimulant.

Devices and Systems

Also included are devices for performing aspects of the subject methods. The subject devices may include, for example, electrophoresis apparatus, ultrasounds, microwaves, needles, tubing, perfusion pumps, flow-assisted clearing devices etc., for fixing, clearing, and/or staining specimens.

Clearing Device

A device suitable for use in carrying out the subject methods is an electrophoresis device for use in removing cellular components from a specimen, e.g., cellular components that are not crosslinked to the hydrogel network. By "electrophoresis" it is meant the application of an electric field to a sample, e.g., to a biological sample. Electrophoresis is most commonly used to mobilize biological macromolecules, e.g., nucleic acids, proteins, in a sample to separate and analyze those macromolecules. Numerous electrophoretic techniques have been developed including capillary electrophoresis, gel electrophoresis, paper electrophoresis, and immunoelectrophoresis. For example, in gel electrophoresis, a hydrogel is formed using compounds such as agarose or polyacrylamide. A mixture containing the desired macromolecules is placed (or loaded) onto one end of the gel, and the gel is then placed in contact with a liquid buffer. This liquid buffer contains salts, which, when dissolved, form ions within the buffer. Biological molecules are typically charged, for example when contacted with electrophoresis buffer. For example, DNA is negatively charged in common electrophoresis buffers due to the phosphate groups in its backbone. Therefore, when electric current is applied to the ends of the gel, the biological molecules move through the gel from one end to the other. Examples of electrophoresis devices suitable for use in carrying out the subject methods may be found in, e.g., U.S. Patent Application No. 20150144490, the disclosure of which is incorporated herein by reference.

Electrophoresis devices suitable for use in the subject methods will generally comprise an electrophoresis chamber into which a buffer solution and the hydrogel-embedded specimen may be placed. The electrophoresis chamber may generally be any suitable size to accommodate a hydrogel-embedded sample of interest, and may be constructed of any material that will retain solution within the chamber, for example glasses and plastics, such as, for example, acrylics, polycarbonates, polystyrenes, polymethyl methacrylates, polyethylene, polyfluoroethylene, polypropylene, polyurethane, polyethylene terephthalate, polytetrafluoroethylene and the like. In some embodiments, a chamber may be molded or machined or otherwise formed from a resin or hard plastic, as appropriate for particular applications. In certain embodiments, an electrophoresis chamber may further comprise a component that is configured to support a hydrogel-embedded sample, such as, e.g., a platform, within the electrophoresis chamber.

In some embodiments, an electrophoresis device may include a lid that fits over the electrophoresis chamber to close the chamber. Lids in accordance with embodiments of the invention may include a seal that forms a liquid-tight and/or air-tight seal with the body of the electrophoresis chamber when the lid is coupled to the chamber. In some embodiments, one or more sealing components may be attached to the lid, attached to the chamber, or attached to both the lid and the chamber. When the lid is coupled to the chamber, the sealing components may form a liquid and/or air-tight seal.

In certain embodiments, an electrophoresis chamber may be partitioned by, e.g., a solid divider or by air into two distinct regions, where each region comprises one electrode in a buffer, and the specimen is positioned within the buffer such that the specimen spans, or straddles the two regions, such that the electric field created by the electrodes is created through the specimen. In some instances, the chamber may comprise a platform or support structure, upon or into which the hydrogel-embedded specimen is placed, e.g., a platform between two electrodes, a platform that spans regions of the chamber comprising the electrodes, etc.

The electrophoresis apparatus may be operably linked to a power source from which voltage may be applied to the electrodes. In some instances, the power source may be separate from the electrophoresis apparatus, i.e. the electrophoresis apparatus may be a separate module from the power source. In other instances, the power source may be integrated into the electrophoresis apparatus, i.e., the electrophoresis apparatus will comprise the power source.

Flow-Assisted Clearing Device

In certain aspects, subject methods may be performed using a flow-assisted clearing device. A flow-assisted clearing device as described below is not an electrophoresis apparatus. The use of a flow-assisted clearing device bypasses the need for specialized equipment such as an electrophoresis apparatus or a perfusion apparatus. In some cases, a flow-assisted clearing device may comprise a sample chamber, a sample holder removably placed inside the sample chamber, and a buffer circulator, all operably linked to each other. In other cases, a flow-assisted clearing device may comprise a container, a sample holder removably placed inside the container, and a buffer circulator, all operably linked to each other. In some cases, a buffer circulator is temperature controlled and may be any of the circulators described below, or may be a heated stirring plate (e.g., temperature controlled plate that provides an external magnetic field used to control the rotation of a magnetic rod within a container.

In some cases, a flow-assisted clearing device comprises a sample chamber, a sample holder removably placed inside the sample chamber, and a buffer circulator all operably linked to each other. In some cases, a flow-assisted clearing device comprises one or more, e.g., two, three, four, five, six, seven, eight, nine, ten or more sample chambers, a sample holder removably placed inside each sample chamber, and a buffer circulator all operably linked to each other. Each component of a flow-assisted clearing device may be operably linked to each other via tubing that allows the flow of circulated buffer. For example, a tube having a first and second end may be removably attached to both a first and second port of a first and second sample chamber (e.g., a first end on a first sample chamber, and a second end on a second sample chamber).

Sample Chamber

Devices (e.g., flow-assisted clearing devices) suitable for use in the subject methods will comprise a sample chamber into which a buffer flows through and a sample holder containing a hydrogel-embedded specimen may be placed. See, for example FIG. 1J. The sample chamber may be constructed of any material that will retain solution within the chamber, for example glasses and plastics, such as, e.g., acrylic, polycarbonates, polystyrenes, polymethyl methacrylate, polyethylene polyfluoroethylene, polypropylene polyurethane, polyethylene terephthalate, polytetrafluoroethylene and the like. In some aspects, a sample chamber may be molded or machined or otherwise formed from a resin or hard plastic, as appropriate for particular applications. In other aspects, a sample chamber may be constructed of a material that does not allow light to pass through, in the case of photosensitive applications. In some cases, the sample chamber may be covered in a material that does not allow light to pass through (e.g., aluminum foil, etc.).

In some instances, a sample chamber comprises a platform, upon or into which a hydrogel-embedded specimen is placed. In some cases, a sample chamber comprises a platform, upon or into which a sample holder is placed. The sample chamber can be of any size and dimensions. In some cases, a sample chamber is large enough such that a sample holder can be removably placed inside it. In other cases, a sample chamber is large enough such that more than one, e.g., two, three, four, five, six, seven, eight, nine, ten or more sample holders can be removably placed inside it.

A sample chamber of the present disclosure comprises a first and second port (e.g., an inlet and an outlet) configured such that the first port delivers a buffer into the sample chamber (e.g., the inlet), and the second port draws the buffer out of the sample chamber (e.g., the outlet). This configuration allows for a unidirectional flow of the buffer through the sample chamber. In some cases, a sample chamber is operably linked to other components of a flow-assisted clearing device (e.g., buffer circulator, buffer reservoir, buffer filter, etc.) via tubing. For example, a tube with a first and second end may be removably attached to a first port of a sample chamber (e.g., inlet) and to a port of a buffer circulator. A second tube with a first and second end may be removably attached to a second port of the sample chamber (e.g., outlet) and to a second port of a buffer circulator. In this set up, the tubing allows for buffer to enter the sample chamber through the inlet and exit the sample chamber through the outlet, and enter the buffer circulator to become recirculated back into the sample chamber.

In some embodiments, a sample chamber comprises a removably attached lid. The lid can be attached in any known and suitable manner so that it can be removed from the chamber when desired. In some cases, the lid is attached to the chamber by intermittent longitudinal slits. In some cases, the lid is screwed onto the chamber, or is attached to the chamber by a fastening clasp. In other aspects, a removably attached lid when attached to the sample chamber forms an air-tight seal such that no liquid can escape the chamber through the lid. In some cases, a sample chamber may further comprise a sealing ring such that when the lid is attached, an air-tight seal is formed between the lid and the chamber.

In some aspects, a sample chamber of the present disclosure comprises a container with a removably attached lid, and a sample holder that can be removably placed into the container. In such an embodiment, a sample holder comprises strategically placed holes and perforations such that a unidirectional flow of buffer through the sample holder can be achieved.

Referring now to FIG. 1I, an embodiment of a sample chamber 110 is depicted. The depicted sample chamber includes an inlet 111 and an outlet 112. A person of skill in the art will recognize and be able to determine the positioning of the inlet and the outlet relative to the sample chamber to provide a unidirectional flow of buffer inside the sample chamber. The depicted sample chamber also includes a removably attached lid 113.

Referring now to FIG. 1K, an embodiment of an open sample chamber 310 (i.e., with the lid removed) is depicted. The depicted open sample chamber includes an inlet 311 and an outlet 312, and also includes a first 313 and second sample holder 314 removably placed within the open sample chamber.

Referring now to FIG. 1L, an embodiment of a flow-assisted clearing device 410 is depicted. The depicted device includes a container 411 with a removably attached lid 412. The depicted device also includes a sample holder 413 with strategically positioned first 414 and second holes 415 that allow for a unidirectional flow of buffer when the magnetic stir bar 416 is activated by an external magnetic field (e.g., stirring plate). The depicted device also depicts a sample 417.

Sample Holder

Aspects of the disclosure provide a sample holder, used to hold a specimen that is to be cleared using a device (e.g., a flow-assisted clearing device) of the present disclosure. In some cases, a sample holder can be removably placed inside a sample chamber. In some cases, a sample holder allows liquids (e.g., clearing buffer) to flow through, thereby immersing a specimen in liquid. In other cases, a sample holder allows a clearing buffer to flow through, thereby immersing a specimen in liquid. Coupled to a buffer circulator, a sample holder allows a clearing buffer to immerse a specimen, and to flow through the specimen in a directional flow as determined by the buffer circulator. In some cases, the directional flow of the clearing buffer through the specimen is enough for the rapid clearing of the specimen (e.g., removal of lipids, etc.).

In some cases, a sample holder of the present disclosure may be a simple rectangular or round container comprising a lid. A lid of a sample holder may be opened and closed through a hinge region. In some aspects, a lid of the sample holder may be held substantially closed by, e.g., a fastening clasp, a button, a tying mechanism, etc. A person of skill in the art will recognize that a sample holder of the present disclosure is any container that can securely hold a specimen, and which allows for convenience when placing a specimen into, or remove a specimen from, the sample holder.

In some cases, a sample holder of the present disclosure is made of, e.g., plastic, glass, metal, etc. A sample holder can be made using any material that can withstand the temperatures employed according to any method of the present disclosure. In certain aspects, a sample holder may be perforated, i.e., contains holes and spaces for a buffer (e.g., clearing buffer) to freely enter and exit. In some cases, a sample holder may be made of a porous membrane that allows a buffer to pass through.

A sample holder of the present disclosure may be removably placed inside a sample chamber. As such, in some cases, the dimensions of a sample holder is substantially the same as, or smaller than the inner dimensions of a sample chamber. In some cases, the dimensions of a sample holder is smaller than the inner dimensions of a sample chamber, such that multiple sample holders may be removably placed within a single sample chamber. In certain aspects, the dimensions of a sample holder is such that at least one intact specimen, e.g., two specimens, three specimens, four specimens, five specimens, at least five specimens, at least ten specimens, fifteen specimens or more can be removably placed inside the holder. In cases where multiple specimens are placed within a sample holder of the present disclosure, it may be important to establish a placement strategy in which each specimen may be placed in parallel fashion. In other words, each specimen may be placed in a fashion, such that in a device of the present disclosure, each specimen is constantly exposed to fresh circulating buffer. In some cases, a second specimen would be exposed to buffer that just passed through a first specimen. In other cases, a second specimen would not be exposed to buffer that just passed through a first specimen. In some cases, the placement strategy of multiple specimens within a sample holder ensures rapid clearance of the samples. In some cases, the placement strategy of multiple specimens within a sample holder minimizes the chance of cross-contamination between specimens.

Referring now to FIG. 1J, an embodiment of a sample holder 210 is depicted. The depicted sample holder includes a rectangular box with a removably attached lid 211 at hinge 212. The walls of the sample holder are perforated 213 to allow for a buffer to freely pass through.

Buffer Circulator

In some embodiments, in addition to the components described above, a device may optionally comprise one or more of an outer chamber, a temperature controller, a mixer, a buffer circulator, fluid inlet, or fluid outlet. In some embodiments, the device may comprise a sample chamber that is operably connected to a fluid recirculation system configured to transport fluid into and out of the sample chamber via one or more fluid inlets and outlets. In some embodiments, a sample chamber and sample holder may be in fluid communication with one another via a semipermeable material. In some embodiments, a device comprises one or more buffer circulators in fluid communication with a sample chamber and sample holder. A buffer circulator may be used to replace, replenish, or move buffer within at least a portion of a sample chamber. In some embodiments, a device may comprise a temperature controller. A temperature controller may be used to control the temperature of the fluid in at least a portion of a device of the present disclosure. For instance, a temperature controller may be used to control the temperature of at least a portion of the fluid in the sample chamber of a device. In some embodiments, a device comprises a temperature-controlled buffer circulator which may be used to replace, replenish, or move temperature-regulated buffer within at least a portion of a sample chamber. In some embodiments, a device may comprise a mixer that allows for the mixing of one or more fluid prior to entering a sample chamber and/or the mixing of one or more fluid in one or more sample chambers.

In some instances, it may be desirable to replace or recirculate buffer in the electrophoresis chamber. By "circulated" or "recirculated" buffer it is meant that buffer is removed from the chamber and then returned to the chamber, for example, after passing through a cooling unit (refrigeration unit, ice bath, etc.), a heating unit, a filter, etc. By "replaced" is meant that buffer is removed from the chamber and fresh buffer is added in its place. For example, it may be desirable to control the temperature of the buffer inside the electrophoresis chamber (e.g., to prevent the chamber from reaching temperatures that might cause the hydrogel to depolymerize or the biomolecules in the specimen to denature, e.g., 35° C. or more, 40° C. or more, or 50° C. or more, 60° C. or more, 70° C. or more, 80° C. or more, 90° C. or more, or 100° C. or more); to remove macromolecules from the buffer as they exit the specimen; to vary the ionic strength of the buffer; etc. Towards this end, the electrophoresis apparatus may optionally comprise one or more ports through which buffer may enter and/or exit the chamber. In some instances, the chamber may comprise two or more ports, e.g. a first port through which buffer enters the chamber and a second port through which buffer exits the chamber.

Buffer may be added/removed/recirculated/replaced by the use of the one or more ports and optionally, tubing, pumps, valves, or any other suitable fluid handling and/or fluid manipulation equipment, for example, tubing that is removably attached or permanently attached to one or more components of a device. For example, a first tube having a first and second end may be attached to a first port and a second tube having a first and second end may be attached to a second port, where the first end of the first tube is attached to the first port and the second end of the first tube is operably linked to a receptacle, e.g. a cooling unit, heating unit, filtration unit, waste receptacle, etc.; and the first end of the second tube is attached to the second port and the second end of the second tube is operably linked to a receptacle, e.g. a cooling unit, beaker on ice, filtration unit, waste receptacle, etc.

As another example, one tube having a first and second end may be removably attached to both a first and second port, i.e., the first end of the tube is removably attached to the first port and the second end of the tube is removably attached to the second port, where the tubing is operably linked to, for example, a refrigeration unit (e.g., the tubing passes through the unit), a filter (e.g. the tubing comprises a filter), a buffer reservoir (e.g. the tubing receives replacement buffer from a reservoir via, e.g., a splitter), etc. In some instances, the tubing will also be operably connected to a pump, e.g. a peristaltic pump, an electro-osmotic pump, an oscillatory pump, a diaphragm pump etc., that will facilitate the movement of liquid through the tubing, facilitate the addition/removal/recirculation of buffer from the clearing device, etc. In this way, the clearing device (e.g., flow-assisted clearing device) may be operably connected to a cooling unit, heating unit, filtration unit, buffer reservoirs/receptacles, pump, etc. In some embodiments, a refrigeration unit, heating unit, filtration unit, buffer reservoirs/receptacles, pump, etc. will be integrated into the electrophoresis apparatus. In other words, the clearing device may comprise the refrigeration unit, heating unit, filtration unit, buffer reservoirs/receptacles, pump, etc. In other embodiments, the refrigeration unit, heating unit, filtration unit, buffer reservoirs/receptacles, pump, etc., may be a separate module from the clearing device.

Buffer Filter Component

Devices (e.g., flow-assisted clearing devices) suitable for use in the subject methods may further comprise a buffer filter component. In some cases, where the circulating buffer is reused during the specimen clearing process, the buffer passes through one or more, e.g., two, three, four, five, more than five, buffer filter components. A buffer filter component of the present disclosure substantially filters out all of the cleared cellular components from the hydrogel-embedded specimen. In some cases, a buffer filter component is a standalone component. For example, a buffer filter component may be a standalone buffer filter unit that is operably linked to the clearing device. In other cases, a component of the clearing device comprises a buffer filter component. For example, a tube which a buffer is circulated through may comprise a buffer filter component. As another example, the inlet or outlet of a sample chamber may comprise a buffer filter component.

A buffer filter component comprises a filtration compartment containing a filtration means for receiving a buffer and for treating the buffer. Any known filtration means may be used in a buffer filter component, e.g., a filter membrane that filters out cellular components (e.g., lipids) from the buffer.

Parallelized Devices

Devices (e.g., flow-assisted clearing devices) suitable for use in the subject methods may be parallelized. "Parallelized" as used herein means that the devices are operably connected to each other in a parallel fashion, and not in a serial fashion. Parallelized devices all receive buffer from the same source (e.g., buffer reservoir).

Referring now to FIG. 1M, an embodiment of a parallelized flow-assisted clearing device 510 is depicted. The depicted device includes a first 511, second 512, third 513 and fourth 514 sample chambers connected by tubing 515 in parallel. Arrows depict the direction of the flow of a buffer through the sample chambers, wherein a buffer enters an inlet and exits an outlet of a sample chamber.

Automated Cell Quantification Systems

The present disclosure provides systems for the automated quantification of cells in a biological specimen cleared by the subject methods. The systems of the present disclosure involve the identification and counting of active populations of cells (e.g., active populations of neurons) from a cleared biological specimen (e.g., using a flow-assisted clearing device). Such systems may include image processing circuitry configured to perform the steps as described herein.

Aspects of the invention include systems and devices thereof configured for imaging a biological specimen and for the automated cell quantification of the biological specimen. In some embodiments, the subject systems include a light-sheet fluorescence microscope device, a chamber that holds a mounting media embedded biological specimen, a controller, a processor, and a computer-readable medium comprising instructions that, when executed by the processor, causes the controller to execute a calibration procedure to acquire a plurality of alignment parameters for a sample in the sample chamber, and execute an imaging procedure that utilizes the alignment parameters to generate a three dimensional image of the sample. A system of the present disclosure may further comprise computer-readable medium comprising instructions that, when executed by a processor of the device, causes the execution of the image processing, image registration and image analysis methods as described herein.

Examples of imaging and analysis devices suitable for use in carrying out the subject methods include a CLARITY optimized light-sheet microscope (COLM), which image large intact tissue samples. Such methods involve placing a sample in the sample chamber of an optically homogenous sample manipulation component, performing a calibration procedure to align a light sheet and a detection focal plane of a microscope device at a plurality of locations within the sample to acquire an alignment parameter for each location, performing an imaging procedure to collect an image from each of the plurality of locations within the sample, and constructing a three-dimensional image of the sample using the image from each location. Additional description may be found in, e.g., U.S. Patent Application No. 2017/0068086, the disclosure of which is incorporated herein by reference.

Aspects of the invention include a controller, processor and computer readable medium that are configured or adapted to control or operate one or more components of the subject systems. In some embodiments, a system includes a controller that is in communication with one or more components of the systems, as described herein, and is configured to control aspects of the systems and/or execute one or more operations or functions of the subject systems. In some embodiments, a system includes a processor and a computer-readable medium, which may include memory media and/or storage media. Applications and/or operating systems embodied as computer-readable instructions on computer-readable memory can be executed by the processor to provide some or all of the functionalities described herein.

In some embodiments, a system includes a user interface, such as a graphical user interface (GUI), that is adapted or configured to receive input from a user, and to execute one or more of the methods as described herein. In some embodiments, a GUI is configured to display data or information to a user. In addition to the components of the devices and systems of the present disclosure, e.g., as previously described, systems of the disclosure may include a number of additional components, such as data input devices, e.g., interface ports, keyboards, etc., fluid handling components, power sources, etc., and data output devices, e.g., monitors and/or speakers.

Applications

Using the subject methods, reagents, kits, systems and devices, the ordinarily skilled artisan will be able to prepare any biological tissue for microscopic analysis. Methods, reagents, kits, systems and devices may be used to prepare a specimen from any plant or animal, including but not limited to transgenic animals, e.g., vertebrate or invertebrate, e.g. insect, worm, xenopus, zebrafish, mammal, e.g. equine, bovine, ovine, canine, feline, murine, rodent, non-human primate or human. Tissue specimens may be collected from living subjects (e.g., bipsy samples) or may be collected from dead subjects (e.g., autopsy or necrospsy samples). The specimens may be of any tissue type, e.g. hematopoietic, neural (central or peripheral), glial, mesenchymal, cutaneous, mucosal, stromal, muscle (skeletal, cardiac, or smooth), spleen, reticulo-endothelial, epithelial, endothelial, hepatic, kidney, pancreatic, gastrointestinal, pulmonary, fibroblast, and other cell types. In some instances, the specimen is the entire organism, e.g. a worm, an insect, a zebrafish. In other instances, the specimen is a whole organ, e.g., the whole brain of a rodent. In other instances, the specimen is a portion of an organ, i.e. a biopsy, e.g. a biopsy of a transplanted tissue. The specimen may be freshly isolated or preserved, e.g. snap frozen. In some embodiments, the specimen may be a previously preserved specimen, such as, e.g., a preserved specimen from a tissue bank, e.g., a preserved specimen of a human brain obtained from a tissue collection program. In some instances, a specimen may be from a subject known to suffer from a specified disease or condition, such as, e.g., a sample of brain tissue from an autistic human. In other instances, a sample may be from a "normal" subject that does not suffer from a specific disease or condition. In some instances, a sample may be from a transgenic subject, such as, e.g., a transgenic mouse.

Because the cells of the specimen are crosslinked to a hydrogel that physically supports the ultrastructure of the tissue, cellular components, e.g. lipids, that normally provide structural support but that hinder visualization of subcellular proteins and molecules may be removed while preserving the 3-dimensional architecture of the cells and tissue. This removal renders the interior of biological specimen substantially permeable to light and/or macromolecules, allowing the interior of the specimen, e.g. cells and subcellular structures, to be microscopically visualized without time-consuming and disruptive sectioning of the tissue. The procedure is also more rapid than procedures commonly used in the art, as clearance and permeabilization, typically performed in separate steps, may be combined in a single step of removing cellular components. Additionally, the specimen can be iteratively stained, unstained, and re-stained with other reagents for comprehensive analysis.

The subject methods find many uses. For example, the subject methods may be applied to preparing specimens for the study of the connectivity of the central nervous system. "Connectivity" as used herein generally means the connections between neurons, and includes connections at the single cell level, e.g., synapses, axon termini, dendritic spines, etc., as well as connections between groups of neurons and regions of the CNS as major axon tracts, e.g., corpus callosum (CC), anterior commissure (AC), hippocampal commissure (HC), pyramidal decussation, pyramidal tracts, external capsule, internal capsule (IC), cerebral peduncle (CP), etc. A whole brain and/or spinal cord specimen or region thereof (e.g. cerebrum (i.e. cerebral cortex), cerebellum (i.e. cerebellar cortex), ventral region of the forebrain (e.g. striatum, caudate, putamen, globus pallidus, nucleus accumbens; septal nuclei, subthalamic nucleus); regions and nuclei of the thalamus and hypothalamus; regions and nuclei of the deep cerebellum (e.g dentate nucleus, globose nucleus, emboliform nucleus, fastigial nucleus) and brainstem (e.g. substantia nigra, red nucleus, pons, olivary nuclei, cranial nerve nuclei); and regions of the spine (e.g. anterior horn, lateral horn, posterior horn)) may be prepared post-mortem by the subject methods and the connectivity of the neurons therein microscopically analyzed, e.g. obtained, stored, rendered, used, and actuated, e.g. to provide the full connectivity of a brain, e.g. a human brain, after death. Such studies will contribute greatly to the understanding of how the brain develops and functions in health and during disease, and of the underpinnings of cognition and personality.

As another example, the subject methods may be employed to evaluate, diagnose or monitor a disease. "Diagnosis" as used herein generally includes a prediction of a subject's susceptibility to a disease or disorder, determination as to whether a subject is presently affected by a disease or disorder, prognosis of a subject affected by a disease or disorder (e.g., identification of cancerous states, stages of cancer, likelihood that a patient will die from the cancer), prediction of a subject's responsiveness to treatment for a disease or disorder (e.g., a positive response, a negative response, no response at all to, e.g., allogeneic hematopoietic stem cell transplantation, chemotherapy, radiation therapy, antibody therapy, small molecule compound therapy) and use of therametrics (e.g., monitoring a subject's condition to provide information as to the effect or efficacy of therapy). For example, a biopsy may be prepared from a cancerous tissue and microscopically analyzed to determine the type of cancer, the extent to which the cancer has developed, whether the cancer will be responsive to therapeutic intervention, etc.

In such methods, tissue specimens can be prepared and analyzed at two different time points and results compared to monitor a disease progression and advancement. In the context of monitoring a disease, the methods also contemplate monitoring a disease in response to treatment and/or therapy. For example, a specimen may be analyzed prior to administration of a treatment and/or therapy and a second specimen analyzed after administration of a treatment and/or therapy. The results of the two time points may then be compared to determine efficacy of treatment.

As another example, a biopsy may be prepared from a diseased tissue, e.g. kidney, pancreas, stomach, etc., to determine the condition of the tissue, the extent to which the disease has developed, the likelihood that a treatment will be successful, etc. The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. The terms "individual," "subject," "host," and "patient," are used interchangeably herein and refer to any mammalian subject for whom diagnosis, treatment, or therapy is desired, particularly humans. Examples of diseases that are suitable to evaluation, analysis, diagnosis, prognosis, and/or treatment using the subject methods and systems include, but are not limited to, cancer, immune system disorders, neuropsychiatric disease, endocrine/reproductive disease, cardiovascular/pulmonary disease, musculoskeletal disease, gastrointestinal disease, and the like.

Similarly, the subject methods may be used to monitor tissue grafts to determine how well the subject has accepted a transplanted organ/tissue, e.g. heart, kidney, liver, or other organ. In such instances, a biopsy of the transplanted organ may be prepared by the subject methods, and the specimen microscopically analyzed for, e.g., tissue integrity, tissue vascularization, the infiltration of immune cells, etc.

The subject methods may also be used to evaluate normal tissues, organs and cells, for example to evaluate the relationships between cells and tissues of a normal tissue specimen, e.g., a tissue specimen taken from a subject not known to suffer from a specific disease or condition. The subject methods may be used to investigate, e.g., relationships between cells and tissues during fetal development, such as, e.g., during development and maturation of the nervous system, as well as to investigate the relationships between cells and tissues after development has been completed, e.g., the relationships between cells and tissues of the nervous systems of a fully developed adult specimen. In some embodiments, the subject methods may be used on samples collected from transgenic animals to investigate the effects of genetic changes on the development and/or function of specific cells, tissues, and/or organs.

The subject methods also provide a useful system for screening candidate therapeutic agents for their effect on a tissue or a disease. For example, a subject, e.g. a mouse, rat, dog, primate, human, etc. may be contacted with a candidate agent, an organ or a biopsy thereof may be prepared by the subject methods, and the prepared specimen microscopically analyzed for one or more cellular or tissue parameters. Parameters are quantifiable components of cells or tissues, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Read-outs may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. Thus, for example, one such method may comprise detecting cellular viability, tissue vascularization, the presence of immune cell infiltrates, efficacy in altering the progression of the disease, etc. In some embodiments, the screen includes comparing the analyzed parameter(s) to those from a control, or reference, sample, e.g., a specimen similarly prepared from a subject not contacted with the candidate agent. Candidate agents of interest for screening include known and unknown compounds that encompass numerous chemical classes, primarily organic molecules, which may include organometallic molecules, inorganic molecules, genetic sequences, etc. Candidate agents of interest for screening also include nucleic acids, for example, nucleic acids that encode siRNA, shRNA, antisense molecules, or miRNA, or nucleic acids that encode polypeptides. An important aspect of the invention is to evaluate candidate drugs, including toxicity testing; and the like. Evaluations of tissue samples using the subject methods may include, e.g., genetic, transcriptomic, genomic, proteomic, and/or metabolomics analyses.

The subject methods may also be used to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, ancestry, and the like. Such detection may be used in, for example, diagnosing and monitoring disease as, e.g., described above, in personalized medicine, and in studying paternity.

EXAMPLES

Materials and Methods:
Animals

Male and female C57BL/6J mice were group-housed on a reverse 12 h light/dark cycle. Mice were 6 to 8 weeks old at the time of viral infusion. Food and water were given ad libitum. Ai14 mice and wild type C57BL/6 mice were purchased from JAX. Rosa26$^{loxp\text{-}stop\text{-}loxp\text{-}eGFP\text{-}L}$10 (originally named TRAP (translating ribosome affinity purification); renamed to rTag here to differentiate from the other ArcTRAP used in this study (Targeted Recombination in Active Populations)) mice were from Dr. Evan Rosen at Harvard Medical School. Male mice were used in all behavioral assays. Both male and female mice were used for histology and anatomy assays. All experimental protocols were approved by the Stanford University Institutional Animal Care and Use Committee and were in accordance with the guidelines from the National Institutes of Health.
Virus and Injection Adeno-associated viral (AAV) vectors were serotyped with AAV5 or AAV8 coat proteins and packaged by the University of North Carolina Vector Core and Stanford University Vector Core. Injections were made unilaterally into the PFC with final viral concentrations of AAV8-fos-ER$^{T2}$-Cre-ER$^{T2}$-PEST: $3 \times 10^{12}$, AAV8-CaMKIIα-EYFP-NRN: $1.5 \times 10^{12}$, AAV5-fosCh-YFP: $2 \times 10^{12}$, AAV5-CaMKIIα-YFP: $1.5 \times 10^{11}$, all as genome copies per mL.
Constructs and Virus The pAAV-fos-ChR2-EYFP (fosCh) plasmid was constructed by fusing the codon-optimized ChR2 (H134R) tagged with enhanced yellow fluorescent protein to a truncated c-fos gene sequence that included the 767 bp minimal promoter segment and the 500 bp intron 1 coding region containing key regulatory elements. A 70 bp PEST sequence was inserted at the C-terminal end to promote degradation and thereby prevent the membrane targeted ChR2-YFP from accumulating over time. The construct was cloned into an AAV backbone. The pAAV-fos-ER$^{T2}$-Cre-ER$^{T2}$-PEST plasmid was constructed by replacing the ChR2-EYFP in the fosCh plasmids with an ER$^{T2}$-Cre-ER$^{T2}$ cassette. The pAAV-CaMKIIα-EYFP-NRN plasmid was constructed by replacing the 479 bp hGH polyA tail in pAAV-CaMKIIα-eYFP-WPRE-hGHpa with a DNA fragment containing the 992 bp 3' UTR of Neuritin plus 215 bp bGH poly A flanked by AfeI and BstEI sites (NRN from the 3' UTR of the rat neuritin mRNA, (NM_053346.1)).
Stereotaxic Surgery 6-7-week-old mice were anaesthetized with 1.5-3.0% isoflurane and placed in a stereotaxic apparatus (Kopf Instruments). Surgeries were performed under aseptic conditions. A scalpel was used to open an incision along the midline to expose the skull. After performing a craniotomy, viruses (specific titer and volume for each virus can be found in the virus preparation section) was injected into the mPFC using a 10 µl nanofill syringe (World Precision Instruments) at 0.1 µl min−1. The syringe was coupled to a 33 gauge beveled needle, and the bevel was placed to face the anterior side of the animal. The syringe was slowly retracted 20 min after the start of the infusion. A slow infusion rate followed by 10 min of waiting before retracting the syringe was crucial to restrict viral expression to the target area. Infusion coordinates were: anteroposterior, 1.9 mm; mediolateral, 0.35 mm; dorsoventral, 2.6 mm. Coordinates for the unilateral implantation of fiber optic cannulas (Doric Lenses 200 µm diameter) were: anteroposterior, 1.9 mm; mediolateral, 0.35 mm; dorsoventral, −2.4 mm. All coordinates relative to bregma.
ArcTRAP Labeling Male ArcTRAP (ArcCreER+/−, Ai14+/−) mice were used for study. 6-7 week old ArcTRAP mice were handled and injected with saline daily for at least 5 days prior to the experiment (including the home cage controls) to minimize the labeling due to handling and injections. The mice were 7-8 weeks old at the time of behavioral labeling. On experimental day 0, animals from both cocaine and shock groups were individually placed in a plastic chamber equipped with a grid floor connected to a shock generator, for 10 minutes to acclimatize the animals to the chamber (without receiving any actual shock or cocaine). On the following two days (experimental day 1 and day 2), animals were individually placed in the chamber for 10 minutes right after receiving 15 mg/kg intraperitoneal cocaine (cocaine group) or to receive 20 random foot shocks (2 s, 0.5 mA, 2 shocks per minute on average, shock group). The home cage control group remained in their home cage for the whole period. All the chambers were cleaned with 70% ethanol between trials. On experimental day 2, all mice received 5 mg/kg 4TM (IP injection) 3 hours after the behavioral challenge to enable TRAP labeling. All groups, including the home cage controls, received 4-hyroxytamoxifen injections at the same time of the day (2-3 PM). The bedding of all cages were refreshed daily for 48 hours to prevent 4TM retake. All the labeled mice were kept in their home cage for an additional 10 days to allow the full expression of tdTomoto before perfusion.

Activity-Dependent Ribosome Labeling

Male Arc-rTag mice were trained and labeled with 4TM with the same protocol used in ArcTRAP labeling. After labeling, the mice were returned and kept in their home cage for 14 days to allow full integration of tagged ribosomes.

Delivery of 4-Hydroxytamoxifen

An aqueous formulation (instead of oil, which tends to give slower drug release) is designed to facilitate transient 4TM delivery. 10 mg of 4TM (Sigma H6278) was first dissolved in 250 µl DMSO. This stock is first diluted in 5 ml of saline containing 2% Tween 80 and then diluted 1:1 again with saline. The final injectable solution contained: 1 mg/ml 4TM, 1% Tween 80 and 2.5% DMSO in saline. The pharmacokinetics of 4TM in mouse brain (using the above vehicle) was determined using a standard LS-MS method at Biomaterials and Advanced Drug Delivery Laboratory at Stanford. Briefly, 30 C57BL/6J mice were injected (IP) with 10 mg/kg 4TM at indicated time points (n=5 each time point) and n=5 mice injected with vehicle alone were used as blank control. Brains were collected after perfusion using 1×PBS at different time points and snap-frozen in liquid nitrogen before homogenized for Liquid Chromatography Mass Spectrometry (LC-MS) analysis.

Clarity Processing

The three key features of this new approach were: 1) accelerated clarification through parallelized flow-assisted clearing crucial for large cohorts (FIGS. 1D-1G) independent of specialized equipment such as electrophoresis or perfusion chambers; 2) >90% cost reduction (also important for these large behavioral cohorts) using a new refractive index-matching process; and 3) optical properties such that the whole mouse brain can be imaged using a commercial light-sheet microscope (LSM) under a single field of view (FOV) and as a single stack (~1200 steps across a ~6.6 mm range) in less than 2 hours with single-cell resolution throughout the whole volume (this speed and simplicity is also critical for large behavioral cohorts; FIGS. 2C-2D). Raw data files from each brain are ~12 GB in size and can be easily stored and directly analyzed on standard desktop workstations without the need for compression or stitching.

A hydrogel based on 1% acrylamide (1% acrylamide, 0.125% Bis, 4% PFA, 0.025% VA-044 initiator (w/v), in 1×PBS, Ref) was used for all CLARITY preparations. Mice were transcardially perfused with ice-cold 4% PFA. After perfusion, brains were post-fixed in 4% PFA overnight at 4° C. and then transferred to 1% hydrogel for 48 hours to allow monomer diffusion. The samples were degassed and polymerized (4-5 hours at 37° C.) in a 50 ml tube. The brains were removed from hydrogel and washed with 200 mM NaOH-Boric buffer (pH=8.5) containing 8% SDS for 6-12 hours to remove residual PFA and monomers. Brains could now be transferred to a flow-assisted clearing device using a temperature-control circulator or a simper combination of 50 ml tube and heated stirring plate (FIGS. 1D-1E). 100 mM Tris-Boric Buffer (pH=8.5) containing 8% SDS was used to accelerate the clearing (at 40° C.). Note that Tris-containing buffer should only be used after PFA is completely washed out as Tris has primary amide group that can potentially interact with PFA. With this setup, a whole mouse brain can be cleared in 12 days (with circulator, or 8 days for a hemisphere) or 16 days (with conical tube/stir bar). After clearing, the brain was washed in PBST (0.2% Triton-X100) for at least 24 hours at 37° C. to remove residual SDS. Brains were incubated in a refractive index matching solution (RapidClear, RI=1.45, Sunjin lab, "http://" followed by "www.sun" followed by "jinlab." followed by "com/") for 8 hours (up to 1 day) at 37° C. and then 6-8 hours at room temperature. After the RC incubation, the brains were ready for imaging.

FIG. 1: Behavioral cohort-scale brainwide activity mapping. (FIG. 1A) Pharmacokinetics of 4TM in mouse brain after a single intraperitoneal injection (10 mg/kg); n=5 per time point. (FIG. 1B) Cocaine dosing (15 mg/kg) and a series of foot shocks (0.5 mA/2 s) lead to place preference and aversion, respectively. An independent cohort of mice was used to validate the stimuli used in the study as appetitive (cocaine) and aversive (shock) using a 3-chamber place preference test. After two days of indicated exposure, fold-change in preference for the side where cocaine or shock was given was quantified. n=5 per group, *P<0.05, **P<0.01, unpaired t-test. Error bars, mean±s.e.m. (FIG. 1C) Representative movement tracking data. (FIG. 1D) Setup of parallel flow-assisted clearing. Up to 4 mouse brains can be inserted into a tissue cassette (30×40×12 mm). Two cassettes (indicated by red arrows) are inserted into a chamber constructed with an inlet and outlet for buffer exchange. To scale up clearing, multiple chambers (each containing up to 8 brains) can be connected in parallel to a temperature-controlled circulator (calibrated so that the temperature in the sample chamber is kept at 40° C.). (FIG. 1E) Alternative flow-assisted clearing setup without using a circulator. A 50 ml conical tube (with small holes drilled in the middle and on the bottom, as indicated by red arrows) can be inserted into a 250 ml glass bottle filled with clearing buffer. Each tube fits 3-4 mouse brains. Unidirectional flow (blue line) is created by using a magnetic stir bar and a stirring hot plate to accelerate the clearing. Upon first use, the temperature of the hot plate needs to be set properly so that the buffer temperature is maintained at desired level inside the conical tube. The speed of the stirring should also be set properly so that proper flow is being generated without damaging the sample. (FIGS. 1F-1G) Schematic and picture of the adapter used for mounting brains onto the ultramicroscope (Lavision Biotec). (FIG. 1H) Data processing pipeline for image registration, cell detection, annotation and quantification.

Figure 2:
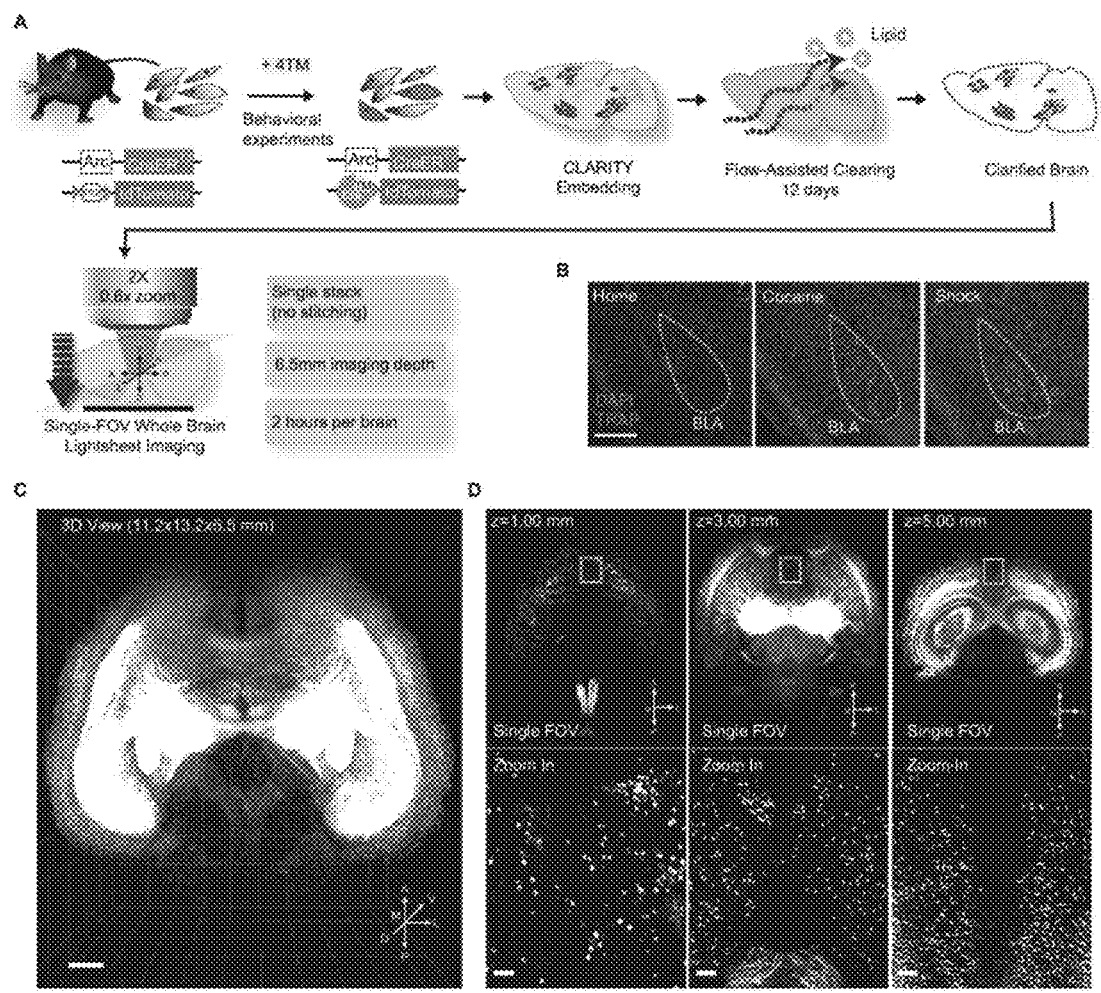
FIG. 2, panels A-D: Schematic showing an embodiment of a cohort-scale sample processing pipeline and images representing light-sheet microscopy images of processed brains.

FIG. 2: Behavioral cohort-scale brainwide activity mapping. (FIG. 2A) Schematic of ArcTRAP labeling and the enhanced cohort-scale CLARITY pipeline for rapid whole brain clearing and imaging. CreER expression is driven by the activity-dependent Arc promoter to mediate 4TM-dependent recombination that permanently labels the active neurons with tdTomato. (FIG. 2B) Representative confocal images from 40 µm sections showing TRAP labeling in BLA (yellow circle). Scale bar: 400 µm. (FIG. 2C) Three-dimensional rendering of a CLARITY-processed whole mouse brain (ArcTRAP) imaged by LSM. Scale bar, 500 µm. (FIG. 2D) Top: single FOV images at indicated imaging depths. Bottom: zoomed in images from the yellow-boxed regions in the top row, showing cellular resolution. Scale bar, 100 µm.

Light-Sheet Imaging

Whole brain and hemisphere images were acquired with the Ultramicroscope II (Lavision Biotec). Samples were mounted to a custom 3D printed holder (FIGS. 1F-1G) using RapidClear Mounting Gel (Sunjin lab). For whole brains (TRAP brains), the brain was mounted with the ventral side on top. For hemisphere, the cut surface (midline of the brain)

was placed in touch with the holder and with the most lateral part on the top. Samples were securely mounted to the holder after mounting gel solidified (~5 minute at 4° C.). Mounted samples were imaged inside an imaging chamber filled with 150 ml of Rapidclear (reusable by periodical filtering). Samples were left in imaging chamber for 20-40 min before imaging to allow the equilibrium of imaging liquid. Brains were imaged using a 2×/0.5 NA objective at 0.6× zoom (whole brain, TRAP) or 0.8× zoom (hemisphere, CAPTURE). Multi-color imaging was enabled by applying filters setting to a supercontinuum white laser (NKT photonics). Samples were with two light sheets (NA=0.144) illuminating from both sides of the sample. Z-step was set to 5.16 µm (at 0.6× zoom) or 4 µm (at 0.8× zoom). Five horizontal focal points were set to each imaging plane for creating a homogeneous field of view.

Image Processing and Visualization

All raw images were acquired as 16-bit TIFF files. The raw images were further processed by blind 3D deconvolution using AutoQuantX3 (Media Cybernetics). The parameters of the deconvolution were based on published methods using a similar light sheet microscope with a few modifications (Tainaka et al, Cell, 159:911-924 (2014)). Briefly, the modality was set to "Multi-photon fluorescence" 3D-blind deconvolution with 20 iterations. Noise was set to zero and using "unfiltered image" as "initial guess". In the expert settings, montage was turned on XY but off on Z, with 30-pixel overlap in XYZ. Other settings such as NA, spacing and magnitude were set based on the actual experiments. Either deconvolved or raw images can be 3D-rendered and visualized using Imaris (Bitplane, v8.1.2), for taking snapshot images and making movies.

Registration and Quantification (TRAP Analysis)

Briefly, after deconvolution, images of the TRAP brains were downsampled 4×, a subset were used to generate an average reference brain, individual samples were nonlinearly registered to that average reference, and then that registration was applied to the locations of individual cells to count cell numbers using an anatomical atlas in the reference space. Registration was performed on the reference (autofluorescence channel) using elastix (Klein et al, IEEE Trans Med Imaging, 29:196-205 (2010)).

Detailed procedures: To initialize the reference, 21 brains and their reflection across the midline axis of the image volume (total of 2*21=42 samples) were globally aligned to the Allen Brain Atlas Nissl-stained volume and then averaged. Each brain was then affine registered to the current average five times, and then resulting registered brains were again averaged to provide the input to the next iteration. Finally, all the brains were nonlinearly registered to the current reference (using an affine transformation as initialization), then averaged, for five iterations.

Each of the experimental samples was then nonlinearly registered to the average reference. Cell locations were detected in deconvolved images using Imaris (v8.1.2 Bitplane). The resulting nonlinear transformation for each brain was applied to every cell location found. Binary mask volumes were made for each brain region in the atlas either manually drawn or from aligned Allen Brain Atlas (manually registered using 30 landmarks, using 3D-slicer "http://" followed by "www.slicer" followed by ".org/") and indices from these mask volumes were used to compute the number of warped cell locations in each anatomical region. Of note, regions where ArcTRAP is known to have strong non-tamoxifen dependent labeling (hippocampus, somatosensory and motor cortex) were excluded. Also, consistent with the original paper, AcrTRAP labeling was mainly in the forebrain; therefore, although sparse signal/changes in the broader midbrain/hindbrain regions were detected, the manual validation and analysis was focused on the forebrain. Principal component analysis was performed in MATLAB on the fold-change values relative to controls of all brain regions containing non-zero values.

Manually-defined brain regions: the 3D reference brain was digitally resliced into coronal sections with 100 µm spacing. Eight regions were drawn onto every coronal section with manually identified boundaries based on Allen Brain Atlas. The 2D contours were then used to generate a 3D surface using Imaris to quantify the cell numbers for each brain region.

Histology

Mice were deeply anaesthetized and transcardially perfused with ice-cold 4% paraformaldehyde (PFA) in PBS (pH 7.4). Brains were fixed overnight in 4% PFA and then equilibrated in 30% sucrose in PBS. 40 µm thick coronal sections were cut on a freezing microtome and stored in cryoprotectant at 4° C. until processed for immunostaining. Free-floating sections were washed in PBS and then incubated for 30 min in 0.3% Triton X-100 (Tx100) and 3% normal donkey serum (NDS). Slices were incubated overnight with 3% NDS and primary antibodies including: rabbit anti-GABA (Sigma A2052 1:200), mouse anti-CaMKIIα (Abcam ab22609 1:200), chicken anti-GFP (Abcam ab13970 1:500), and rabbit anti-NPAS4 (gift from Michael Greenberg, 1:2500). Sections were then washed and incubated with secondary antibodies (Jackson Labs 1:1000) conjugated to donkey anti-rabbit Cy5, anti-mouse Cy3 and anti-chicken FITC for 3 hrs at room temperature. All NPAS4 staining was performed using a TSA-Cy5 amplification system (Perkin Elmer) according to the manufacturer's instructions. Following a 20 min incubation with DAPI (1:50,000) sections were washed and mounted on microscope slides with PVA-DABCO. Confocal fluorescence images were acquired on a Leica TCS SP5 scanning laser microscope using a 40×/1.25 NA oil immersion objective. Serial stack images covering a depth of 20 µm through multiple sections were analyzed by an experimenter blind to treatment condition.

Ribosome Profiling

Immunoaffinity purification of ribosome RNA from mPFC was carried out similarly to a protocol previously described (Sanz et al, Proc Natl Acad Sci USA, 106:13939-'13944 (2009)) with minor modifications. For preparation of anti-GFP-conjugated dynabeads, for each sample 50 µl protein G dynabeads (Life Technologies) was first washed with PBST and then incubated with 2 µl anti-GFP antibody (Abcam, ab290) in a total volume of 200 µl PBST. After incubating for at least 20 min at room temperature, the PBS-T was removed and the tissue lysates were immediately added to the beads, as described below. mPFC tissue was harvested using a 2 mm-diameter tissue punch on freshly cut 2 mm-thick coronal sections (cut using pre-chilled brain matrix). mPFC from 5 brains were pooled into one tube and then manually dounce-homogenized in 1 ml of IP buffer [50 mM Tris, pH 7.5; 12 mM MgCl2; 1% NP-40; 100 µg/ml cycloheximide (Sigma); 0.5 mM DTT; 100 mM KCl; 1×HALT protease inhibitor EDTA-free (Thermo); 1 mg/ml sodium heparin (Sigma); 0.2 units/µl RNasin (Promega)]. Following vortexing and centrifugation (12,000×g for 10 min), 50 µl of the supernatant was taken as "input", and the remaining supernatant was incubated with the anti-GFP conjugated dynabeads for immunoprecipitation (IP fraction). After 2 h at 4° C., dynabeads were separated and washed twice with 1 ml high salt buffer [50 mM Tris, pH 7.5;

12 mM MgCl2; 1% NP-40; 100 μg/ml cycloheximide (Sigma); 0.5 mM DTT; 300 mM KCl]. Following the last wash, TRIzol (500 μl, Life Technologies) was immediately added to the beads (IP fraction). Another 500 μl TRIzol was added to the 50 μl input fraction collected earlier. RNA was purified using RNeasy Micro Kit (Qiagen) according to the manufacturer's instructions. RNA samples (all at 100 ng per sample) were processed at the Stanford Protein and Nucleic Acid Biotechnology Facility by one-cycle target preparation, labeling and hybridization to Mouse Gene 2.0 ST Array (Affymetrix), according to the manufacturer's protocol and analyzed by Affymetrix Transcriptiome Analysis Console.

QPCR and Gene Expression Analysis

For qPCR analysis, RNA was reverse transcribed using the ABI high capacity cDNA synthesis kit and used in quantitative PCR reactions containing SYBR-green fluorescent dye (ABI). Relative expression of mRNAs was determined after normalization with TBP levels using the ΔΔCt method.

Cell Culture and In Vitro Activity Testing

Primary cultured hippocampal neurons were prepared from P0 Spague-Dawley rat pups and grown on glass coverslips as previously described. At 12 div cultures were transfected with 1 μg fosCh DNA using calcium phosphate. Immediately following the transfection procedure, cultures were returned to Neurobasal-A culture media (Invitrogen Carlsbad, Calif.) containing 1.25% FBS (Hyclone, Logan, Utah), 4% B-27 supplement (GIBCO, Grand Island, N.Y.), 2 mM Glutamax (GIBCO), and FUDR (2 mg/ml, Sigma, St. Louis, Mo.) to maintain high basal levels of intrinsic synaptic activity, or they were incubated in unsupplemented Neurobasal media that contained 1 μM tetrodotoxin (TTX), 25 μM 2-amino-5-phosphonopentanoic acid (APV) and 10 μM 2,3-dihydroxy-6-nitro-7-sulfamoyl-benzo[f]quinoxaline-2,3-dione (NBQX) to silence electrical activity. Cultures were stimulated for 30 min by exchanging the media with 60 mM isotonic KCl solution and then fixed with 4% PFA at indicated time points.

In Vivo Optrode Recording

Simultaneous optical stimulation and extracellular electrical recording were performed in isofluorane-anesthetized mice. Optrodes consisted of a tungsten electrode (1 MΩ; 125 μm outer diameter) glued to an optical fiber (300 μm core diameter, 0.37 N.A.), with the tip of the electrode projecting beyond the fiber by 300-500 mm. The optical fiber was coupled to a 473 nm laser and 5 mW light measured at the fiber tip was delivered at 10 Hz (5 ms pulses). Signals were amplified and band-pass filtered (300 Hz low cut-off, 10 kHz high cut-off) before digitizing and recording to disk. pClamp 10 and a Digidata 1322A board were used to both collect data and generate light pulses through the fiber. The recorded signal was band pass filtered at 300 Hz low/5 kHz high (1800 Microelectrode AC Amplifier). Stereotaxic guidance was used for precise placement of the optrode, which was lowered through the dorsal-ventral axis of the mPFC by 50 μm increments. The percentage of sites yielding light-evoked action potential firing was determined.

Real-Time Conditioned Place Preference

Behavioral experiments were performed 2 weeks after virus injections during the animals' dark (active) cycle. For induction of fosCh expression under appetitive or aversive conditions, mice received either i.p. injections of cocaine (15 mg/kg) or they underwent 20 random foot shocks (2 s, 0.5 mA, 2 shocks per minute on average). Mice were exposed to appetitive or aversive training twice a day over 5 consecutive days. Conditioned place preference (CPP) was conducted within 12-16 hours after the last appetitive or aversive training. The CPP apparatus consisted of a rectangular chamber with one side compartment measuring 23 cm×26 cm with multicolored walls, a central compartment measuring 23 cm×11 cm with white plexiglass walls, and another side compartment measuring 23 cm×26 cm with distinctive striped walls. Chamber wallpapers were selected such that mice did not display average baseline bias for a particular chamber, and any mouse with a strong initial preference for a chamber was excluded (more than 5 min difference spent in the side chambers during the baseline test). Automated video tracking software (BiObserve) was used to monitor mouse location over 3 consecutive 20 min blocks to assess place preference behavior before, during and after optogenetic stimulation of the fosCh labeled cells. During the light stimulation block, the laser was automatically triggered upon mouse entry into a pre-designated chamber (fully counterbalanced for side) to deliver 2 sec bursts of 10 Hz light pulses every 5 sec (5 ms pulses at 5 mW) for the duration that the mouse remained in the stimulation side. Data are expressed as fold-change in time spent in the light-paired side relative to the initial baseline preference.

Statistics

Two-way ANOVAs were used to assess how gene expression or behavior was affected by other factors (e.g. neuronal activity, optogenetic manipulations). If a statistically significant effect was observed, post hoc testing with correction for multiple comparisons was performed using Tukey's multiple comparisons test. Unpaired t-tests were used for comparisons between two groups. Two-tailed tests were used throughout with $\alpha=0.05$. Multiple comparisons were adjusted with the false discovery rate method. The experimenter was blinded to the experimental groups while running behavioral experiments and analyzing images. In all figure legends n refers to biological replicates.

Example 1: Behavioral Cohort-Scale Whole-Brain Activity Mapping

The ArcTRAP transgenic mouse line was previously shown to translate temporally delimited neuronal activity into permanent fluorescence (tdTomato) via CreER/Tamoxifen-mediated recombination (FIG. 2A). While the ArcTRAP line had also been reported to be associated with problematic background recombination, a novel aqueous formulation of the fast-acting tamoxifen (4-hydroxytamoxifen, 4TM) was developed, enabling dosage reduction by an order of magnitude; this new approach to ArcTRAP was found to eliminate the background recombination (FIG. 2B; FIG. 1A). ArcTRAP mice under these conditions can be exposed to a rewarding or aversive experience (cocaine dosing at 15 mg/kg or a series of 0.5 mA/2 s foot shocks, respectively) with resulting robust labeling of neurons; for example, histology confirmed that both valences of experience (with comparable but opposite conditioning value; FIGS. 1B-1C) efficiently recruited neurons in basolateral amygdala (BLA, known to be involved in both reward and aversion processing) (FIG. 2B).

At this level of inspection, the information provided is not greater than would be made available from single-unit recording or from single-cell $Ca^{2+}$ imaging. Traditional thin-section histology would be prohibitively labor-intensive for whole-brain analysis in large behavioral-scale cohorts of experimental subjects, and also subject to sample loss and sampling bias; the recent emergence of tissue transparency techniques such as CLARITY has in principle enabled lossless high-resolution brain-wide imaging compatible with molecular analysis, if not yet in large cohorts of subjects. Therefore, an enhanced CLARITY process suitable for this challenge of large-cohort analysis linked to behavioral experience was developed; key cohort-scale capabilities achieved included much faster speed and lower cost, as well as novel automated analysis algorithms adapted to both TRAP labeling and widely-available commercial light sheet microscope (LSM) hardware (FIGS. 2A, 2C, 2D; FIGS. 1D-1G).

Employing this integrated TRAP/CLARITY approach, multiple behavioral-scale brain cohorts (with temporally-delimited exposure to appetitive cocaine dosing, aversive foot shock or neither experience; n=5 mice per group) were processed using two-color imaging on the LSM. Image volumes taken in the green (autofluorescence) channel were iteratively co-registered, using a novel intensity-based non-linear registration algorithm, to generate an average reference brain. The registration based on the green channel from each brain was then used to warp the red channel (consisting of the TRAP signal) for each brain into this reference space (FIG. 1H).

Multiple potentially-relevant regions in the reference brain, including mPFC, NAc (nucleus accumbens), BLA, BNST (bed nucleus of the stria terminalis), LHA (lateral hypothalamus), PVN (paraventricular nucleus of hypothalamus) and CeA (central nucleus of the amygdala), were first manually delineated. At this level of inspection, the singly-defined regional levels of neuronal activation were found to be largely similar between the two very different kinds of experience (FIGS. 3A-3D, FIGS. 4H-4J), highlighting the need for more refined analysis. To search for patterns in cell labeling that could differentiate the two conditions despite this apparent similarity, the Allen Brain Atlas (ABA) was manually registered to the CLARITY reference. Locations of experience-recruited (tdTomato-expressing) cells were also mapped into the reference space, so that the number of recruited cells in every brain region could be quantified in unbiased fashion; changes in TRAP cell numbers (relative to home cage-animal mean values) in ~200 brain regions were then automatically detected and quantified (FIGS. 4A-4G).

Figure 3:
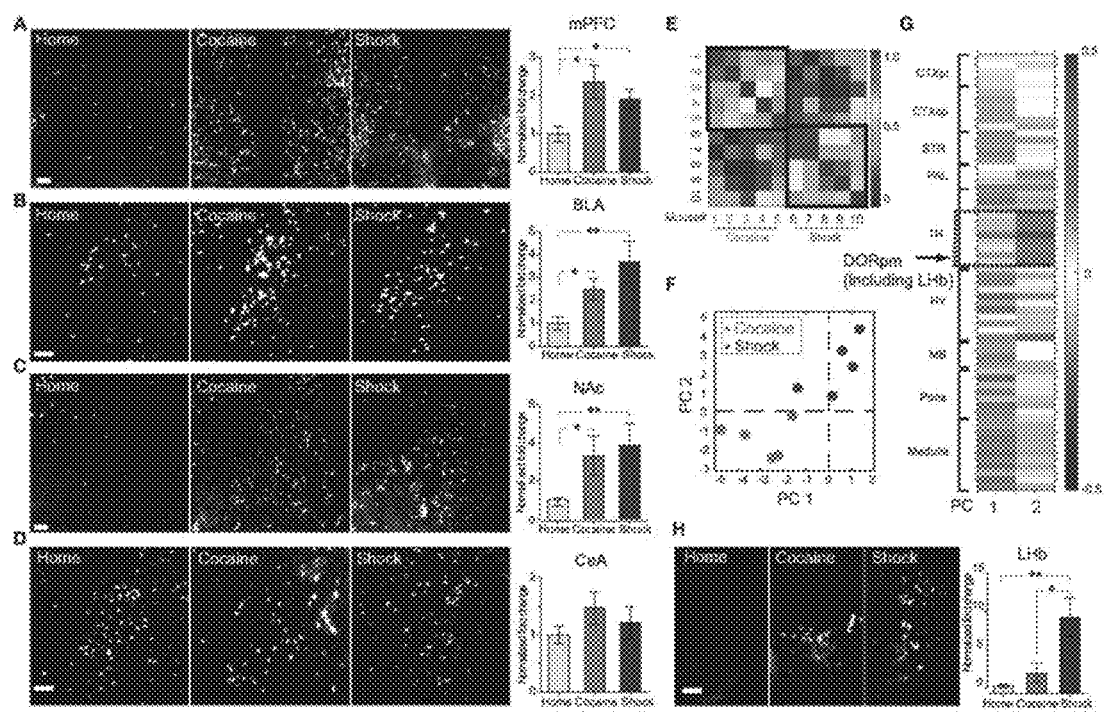
FIG. 3, panels A-H: Data showing cocaine and shock recruit overlapping brain regions.

FIG. 3: Cocaine and shock recruit overlapping brain regions. (FIGS. 3A-3D) TRAP cells in manually annotated regions. Left: representative images taken at the center of the indicated regions (maximum projection of 100 μm volume). Scale bars: 100 μm. Right: fold change in TRAP cell numbers (normalized to home cage). (FIG. 3E) Pearson correlation among the 10 mice, based on the r-value computed from fold-activation changes relative to home cage across all non-zero-containing brain regions. Note the higher brainwide correlation values within behavioral groups (black bounding boxes) compared to across-groups. (FIG. 3F) Locations of individual mice projected into the two-dimensional space of the two principal components comprising the majority of the variance, where the position of each mouse corresponds to the extent to which a particular principal component accounts for that mouse's variance across all brain regions. (FIG. 3G) Principal component coefficients across all the brain areas—the contribution of each brain area to each principal component—were summarized as clusters of proximal regions. Note the distinct region-selective contribution to PC 2 (dashed box; detailed in text). CTXpl/sp: cortical plate/subplate, SRT: striatum, PAL: pallidum, TH: thalamus, HY: hypothalamus, MB: midbrain. DORpm: polymodal association cortex-related dorsal thalamus. (FIG. 3H) Representative image and quantification of TRAP cells in LHb. Scale bar: 100 μm. For all panels, n=5 per group, *P<0.05, **P<0.01, unpaired t-test comparing behavioral group to home cage; # p<0.05, unpaired t-test comparing cocaine versus shock group. All P-values were adjusted for multiple comparisons using the false discovery rate method. Error bars: mean±s.e.m.

Figure 4:
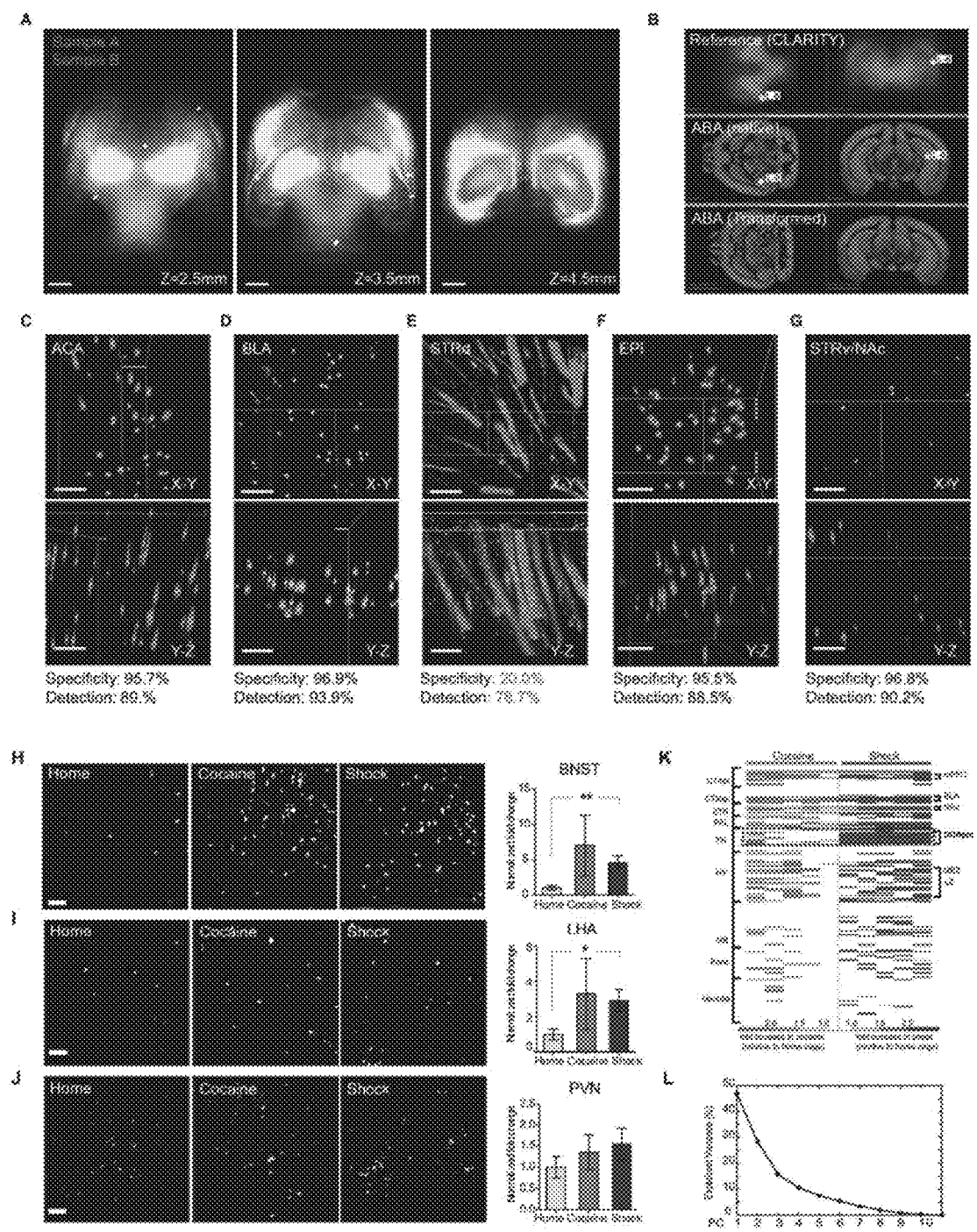
FIG. 4, panels A-L: Images showing the registration, alignment and cell detection and quantification of processed brains.

FIG. 4: Cocaine and shock recruit overlapping brain regions. (FIG. 4A) Representative images illustrating alignment between individual brains after registration. TRAP signal from two individuals (one shown as red, the other as green) overlaid to show alignment. White bars indicate small remaining misaligned boundaries due to combined sources of structural variation and alignment error (~200 μm). Scale bar: 500 μm. (FIG. 4B) Representative images illustrating the manual ABA registration using 3D-Slicer. A total of 30 landmarks (showing one (#8) here) were manually placed in the CLARITY reference (top) and the ABA reference (middle). The program calculated the transform (using thin plate registration) and output the transformed ABA image (bottom). (FIGS. 4C-4G) Representative images illustrating the automatic 3D cell detection in various brain regions. Top: cell detection in x-y plane; Bottom: cell detection in y-z plane. ACA: anterior cingulate cortex; BLA: basolateral amygdala; STRd: dorsal striatum; EPI: epithalamus; STRv/NAc: ventral striatum/nucleus accumbens. Note that cell detection failed in STRd as the program could not distinguish fiber bundles from cell bodies. Therefore the STRd was excluded from all subsequent analysis. For quantifying detection accuracy, in each region, the specificity is defined by the percent of cells correctly detected (True positive/(True positive+False positive)) and detection is defined by percent of ground-truth cells detected (True positive/(True positive+False negative)). Manually identified cells are used as "ground truth". Numbers represent means from three independent counts. Scale bar: 100 μm. (FIGS. 4H-4J) TRAP cells in BNST, LHA and PVN. Left: representative images taken at the center of the indicated regions (maximum projection of 100 μm volume). Scale bar: 100 μm. Right: fold-change in TRAP cell numbers (normalized to home cage). n=5 per group, *P<0.05, unpaired t-test. Error bars, mean±s.e.m. (FIG. 4K) Heat map showing cocaine- and shock-activated brain regions. Each column represents an individual mouse. Each row represents an individual brain region (~200 regions in total). Increase in TRAP cell counts in each region was color-coded as fold changes (red: increase cell counts in cocaine group; blue: increase cell counts in shock group; all normalized to home cage controls). Cocaine or shock activated areas were summarized as clusters of proximal regions. CTXpl/sp: cortical plate/subplate, SRT: striatum, PAL: pallidum, TH: thalamus, HY: hypothalamus, MB: midbrain. DORpm: polymodal association cortex-related dorsal thalamus. MEZ: Hypothalamic medial zone, LZ: Hypothalamic lateral zone. (L) Percentage of total variance explained by each principal component in the PCA.

Individual single-region activation patterns that were consistent across subjects within a group largely agreed with the manual analysis, in both behavioral conditions. For example, robust increases in TRAPped cells were observed in both settings within mPFC, NAc, BLA, pallidal regions (containing BNST) and hypothalamus (medial and lateral) (FIG. S2K). However, the change in active cell count (relative to control) across all individual regions revealed distinct multi-region correlation patterns in mice from the same experimental group, suggesting experience-specific brainwide patterns (FIG. 3E). To investigate these differences, principal component analysis (PCA) was applied to the matrix of activated cell-count changes in cocaine- or shock-treatment mice relative to the control condition. The first two principal components (PCs) comprised >75% of the variance for the dataset (FIG. 4L), and thus were examined more closely. Plotting the position of each mouse in the space defined by the first two PCs revealed a clear separation between the behavioral conditions (FIG. 3F).

To better understand the source of this separation, the PC loadings across all of the included brain areas were examined (FIG. 3G). The first PC was found to reflect more general differences in activated cell recruitment across all regions (e.g. higher mean change across all regions in shock versus control mice; P<0.05, t-test). The second PC, by contrast, revealed a specific correlated group of DORpm (polymodal association cortex-related dorsal thalamus) regions, containing the lateral habenula (LHb), a key nucleus for aversive behaviors. These regions were strongly recruited by shock but not by cocaine, revealing a unique level of selective responsiveness to the aversive experience. Consistently, manual quantification also found that shock but not cocaine selectively activated the LHb (p<0.01 for shock vs. home-cage experience; p<0.05 for shock vs. cocaine experience, FIG. 3H). Thus, this novel behavioral cohort-scale whole-brain TRAP/CLARITY labeling revealed large-scale patterns of neuronal activation, as well as quantitative region-specific activation differences at the cellular level between different experimental conditions.

Example 2: Molecular Signature of Experience-Defined mPFC Neurons: Pre-Existing NPAS4 Population Arc$^{CreER}$ mice were crossed to a Cre-dependent ribosome tagging mouse (Arc$^{CreER/+}$ Rosa$^{loxp\text{-}STOP\text{-}Ioxp\text{-}GFP\text{-}L10A}$, named Arc-rTag) to allow genetic labeling of ribosomes from neuronal populations activated by temporally well-defined stimuli (FIG. 5A). With this approach, the tagged ribosome can be immunoprecipitated (IP) from tissue lysate using an anti-GFP antibody, isolating translating mRNA for molecular analysis. Arc-rTag mice were exposed to either the cocaine or shock experience and injected with 4TM. After labeling, mice were returned to the home cage for two weeks before initiation of mPFC extraction and RNA analysis, a design focused on identifying long-term intrinsic signatures of these populations rather than immediate mRNA expression changes associated with acute exposure to stimuli.

Figure 5:
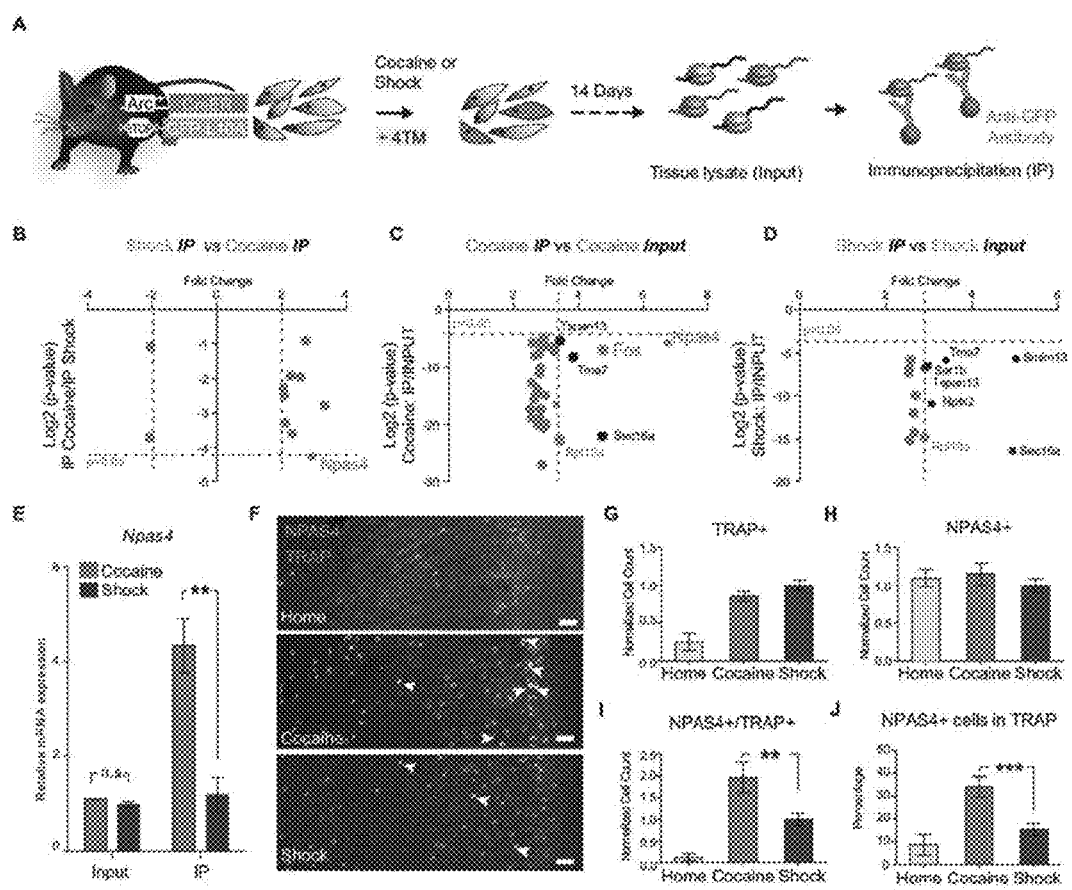
FIG. 5, panels A-J: Schematic showing an activity-dependent ribosome profiling pipeline, and data showing that cocaine preferentially activates NPAS4+ population in mPFC.

FIG. 5: Cocaine preferentially activates the NPAS4+ population in mPFC. (FIG. 5A) Schematic of activity-dependent ribosome profiling. Green: activated neurons; grey: non-activated neurons. (FIGS. 5B-5D) Scatter plot of the most-enriched genes comparing: cocaine-versus shock-activated cells (FIG. 5B), cocaine IP versus cocaine Input (FIG. 5C) and shock IP versus shock Input (FIG. 5D). The bottom right quadrant of each scatter plot, as marked by the dashed green lines, denotes genes with P<0.05 and fold change >2 for the indicated comparisons. As a positive control, the enrichment of RpL10a is highlighted in green. Black dots denote genes that were non-specifically enriched by IP (as shown enrichment in both cocaine and shock IP fraction). (FIG. 5E) Quantitative PCR analysis of Npas4 mRNA expression in the Input and IP fractions. (FIG. 5F) Representative images showing the overlap between TRAP+ and NPAS4+ cells in the mPFC. Scale bar: 100 µm. Arrowheads indicate double positive cells. (FIGS. 5G-5I) Quantification of numbers (normalized to home cage) of TRAP+ (FIG. 5G), NPAS4+ (FIG. 5H) and TRAP+/NPAS4+ (FIG. 5I) cells in the mPFC. (FIG. 5J) Percentage of NPAS4+ cells in TRAP+ cells under three conditions. n=4 per group, *P<0.05, **P<0.01, unpaired t-test. Error bars, mean±s.e.m.

Figure 6:
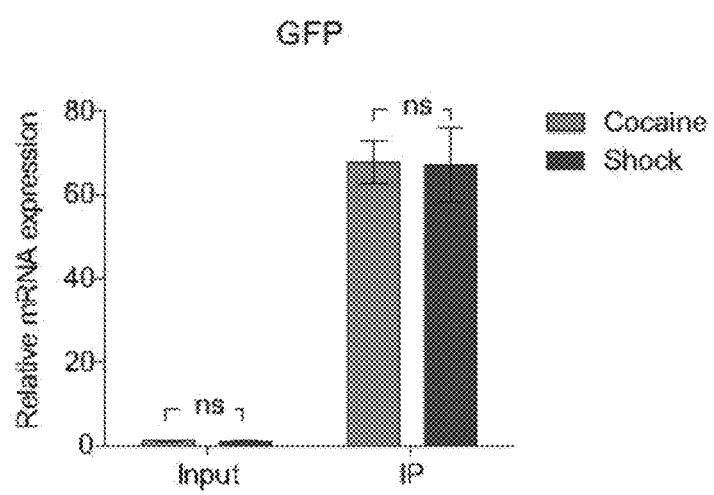
FIG. 6: Data representing quantitative PCR analysis of cocaine and shock-tagged mPFC population.

Translating mRNA from cocaine- and shock-labeled mPFC cells was first analyzed by qPCR to confirm equal enrichment of GFP transcripts under these two conditions (FIG. 6). Four groups of mRNA ("IP fraction" for ribosome-associated transcripts from cocaine and shock, and "Input" for whole-tissue lysate from cocaine and shock) were then analyzed by microarray. For both stimuli, IP fraction groups were enriched 3-fold in the ribosomal-component mRNA (Rpl10a) compared with Input groups (FIGS. 5C-5D), further demonstrating similar levels of mRNA enrichment between cocaine- and shock-activated cells using this approach. Surprisingly, gene expression profiles from cells recruited under the two conditions were highly similar (<10 genes showed >2-fold difference), initially suggesting a single molecular signature; however, a unique transcript, of the activity-dependent transcription factor (Npas4) was strikingly distinct—enriched 3-fold in cocaine-activated cells compared to shock-activated cells (FIG. 5B). This selective enrichment was further confirmed by comparing the IP fraction to the Input from the cocaine-labeled population (FIG. 5C), and finally validated by qPCR analysis (FIG. 5E).

FIG. 6: Cocaine preferentially activates the NPAS4+ population in mPFC. Quantitative PCR analysis of GFP mRNA from the input and IP fraction of the cocaine- and shock-tagged mPFC population. Immunoprecipitation lead to 60-70 fold enrichment of GFP mRNA under both conditions (comparing Input to IP). n=5 per group, ns, P >0.05, unpaired t-test. Error bars, mean±s.e.m.

To test if the enrichment in Npas4 mRNA could relate to general cocaine-elevated Npas4 transcription, Npas4 expression was examined in whole tissue lysates from cocaine- and shock-labeled mPFC. No significant difference was observed (FIG. 5E). Moreover, it was discovered that the number of cells in the mPFC with NPAS4 expression above threshold did not differ between cocaine- and shock-exposed animals, nor between the home-cage and behaviorally-challenged animals (FIGS. 5F-5H). On the other hand, TRAP/NPAS4 double-positive cell counts were significantly higher in cocaine-exposed animals (FIG. 5I), consistent with activity recruitment of an NPAS4 population. Similarly, the percentage of NPAS4+ cells among TRAP+ cells was also significantly higher in cocaine-labeled mPFC than in shock-labeled mPFC (FIG. 5J), confirming that a pre-existing NPAS4+ population is preferentially activated by the cocaine compared with the shock behavioral stimulus.

Example 3: Cocaine- and Shock-Activated Populations Control Appetitive and Aversive Behaviors Having established that mPFC neuronal populations recruited under the appetitive and aversive conditions were separable by gene expression signature and long-range connectivity measures, it was next tested if electrical activity in these two behavioral activity-defined populations had distinct positive or negative conditioning valence for the same animals that had experienced the stimulus, assessed by causal impact on behavior during the place preference task. A codon-optimized channelrhodopsin tagged with EYFP (ChR2-EYFP) under the control of the AAV-cFos backbone described earlier (termed fosCh; FIG. 7A) was used, and stereotaxically injected fosCh into mPFC. For 5 consecutive days these animals were exposed to daily cocaine administration or foot shock behavioral experience. After exposure, a significant increase in the number of fosCh-labeled cells and mean EYFP expression level compared to controls was observed (FIGS. 8A-8C).

Figure 7:
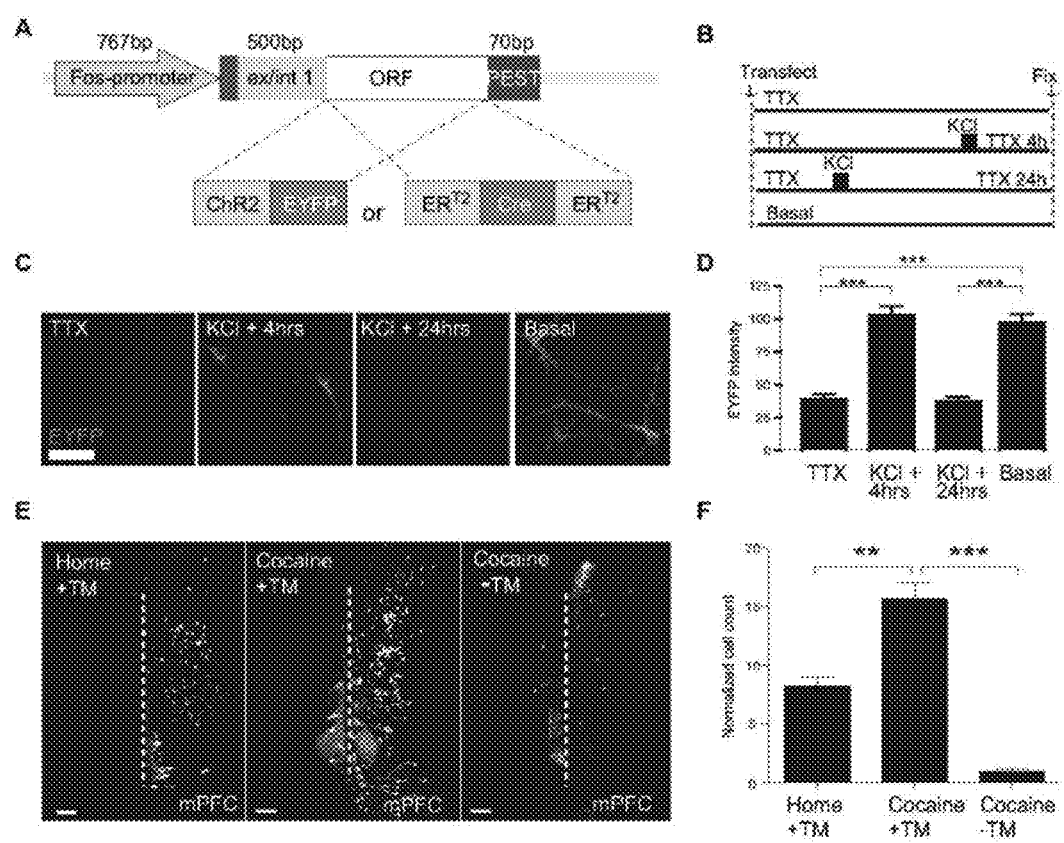
FIG. 7, panels A-F: Schematic showing the strategy of expression cassette construction, and data showing that cocaine and shock-activated mPFC populations have distinct projection targets.

FIG. 7: Distinct projection targets of cocaine and shock-activated mPFC populations. (FIG. 7A) Construction strategy. An expression cassette was inserted immediately after intron 1 of the c-fos gene. Either ChR2-EFYP (cFos-ChR2-EYFP, termed fosCh) or $ER^{T2}$-Cre-$ER^{T2}$ fusion was inserted, followed by a 70 bp PEST sequence to promote construct degradation (to further enhance specificity). (FIG. 7B) Schematic to illustrate treatment of cultured hippocampal neurons following transfection of c-Fos-ChR2-EYFP. Neurons were electrically silenced with TTX, APV and NBQX; fosCh expression was compared to expression levels in "basal" (spontaneously synaptically active, but not otherwise stimulated or silenced) cultures. Following a 30 min depolarizing stimulus (60 mM KCl) the TTX/APV/NBQX solution was replaced and groups were fixed at the indicated time points. (FIG. 7C) Representative images showing fosCh expression of cultured hippocampal neurons for each of the treatment groups. Scale bar: 25 µm. (FIG. 7D) Quantification of mean pixel intensity of EYFP expression for conditions represented in c, n=39-59 cells per group, $F_{3, 205}$=37.20, *P<0.001, ANOVA followed by Tukey's multiple comparison test. (FIGS. 7E-7F) AAV-cFos-$ER^{T2}$-Cre-$ER^{T2}$-PEST was injected into the mPFC of Ai14 Cre-reporter mice. The mice were divided into three groups (n=5 per group): home cage with 4TM, cocaine-injected with 4TM and cocaine-injected without 4TM. (FIG. 7E) Representative images showing 4TM-dependent and activity-dependent labeling of mPFC neurons (tdTomato+), scale bar: 100 µm. (FIG. 7F) Quantification tdTomato+ mPFC cells in three groups (normalized to the No-4TM group). P<0.01, ***D<0.001, unpaired t-test. Error bars, mean±s.e.m.

Figure 8:
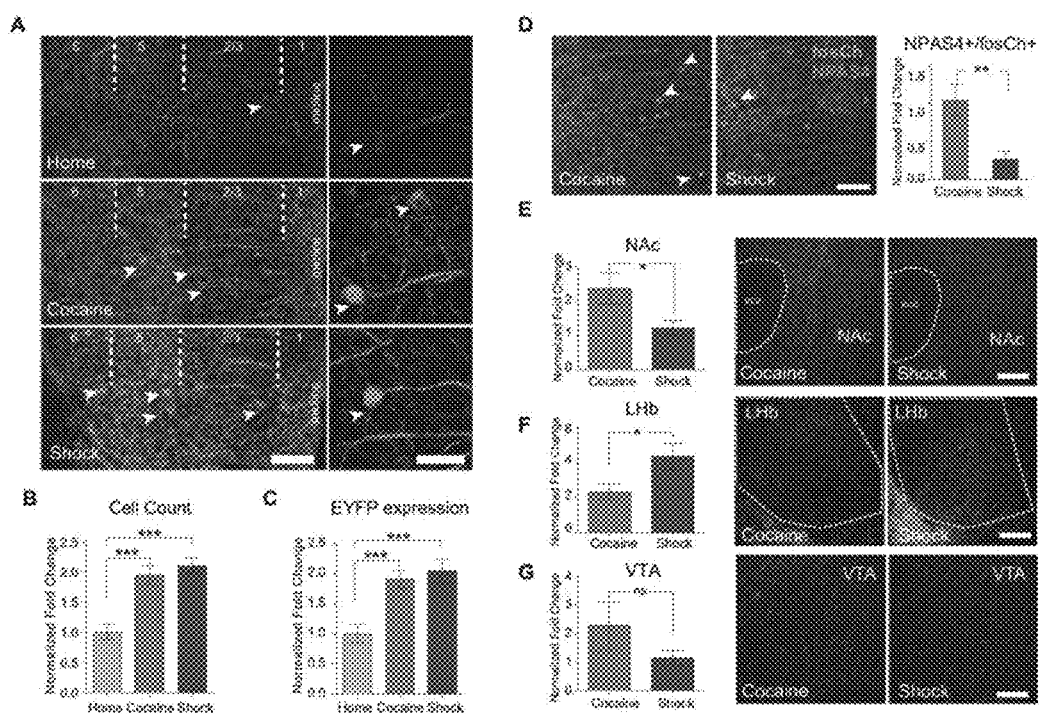
FIG. 8, panels A-G: Data showing the use of fosCh for targeting cocaine and shock-activated mPFC populations.

FIG. 8: Use of fosCh for targeting cocaine- and shock-activated mPFC populations. (FIG. 8A) Representative images showing fosCh expression in mPFC following the indicated behaviors. Left, images visualizing lamina across the cortical depth (midline is on the right). Arrowheads indicate fosCh positive neurons. Scale bars: 100 µm. Right, high-magnification images of individual fosCh neurons. Scale bars: 25 µm. (FIG. 8B) Fold change in fosCh cell numbers (normalized to home cage level). (FIG. 8C) Fold change in mean EYFP fluorescence intensity. n=11-14 per group, *P <0.001, unpaired t-test. (FIG. 8D) Representative images and quantification of fosCh and NPAS4+ cells. Arrowheads indicate double-positive cells. n=5 per group, P<0.01, unpaired t-test. (FIGS. 8E-8G) Left: Comparing density of fosCh projections for cocaine and shock groups. Right: representative images showing the density of fosCh projections in indicated regions. aca: anterior part of anterior commissure. Scale bars: 100 µm. n=11-14 per group, *P<0.05, unpaired t-test. Error bars, mean±s.e.m.

Npas4 expression was first quantified in cocaine- and shock-labeled fosCh cells, and it was hypothesized that cocaine-labeled fosCh cells would exhibit significantly higher Npas4 expression compared with shock-labeled fosCh cells. This was indeed the case (FIG. 8D); importantly, expression of general excitatory or inhibitory neuronal markers did not differ between those two populations (FIGS. 9A-9B). Moreover, consistent with CAPTURE findings, cocaine-labeled fosCh cells were found to project strongly to NAc, while the LHb contained significantly denser EYFP fibers arising from the shock-labeled fosCh cells (FIGS. 8E-8G). Crucially, this method of targeting was sufficiently potent to enable optical control over the resulting sparsely-distributed neuronal subsets; fosCh-labeled cells displayed robust light-evoked firing assessed by in vivo electrophysiological recording (FIGS. 10A-10B). Together, these data demonstrated resolution with the fosCh strategy of the same pattern that had been characterized molecularly and anatomically, and enabled the final test of whether these neuronal subsets were capable of differentially controlling behavior.

Figure 9:
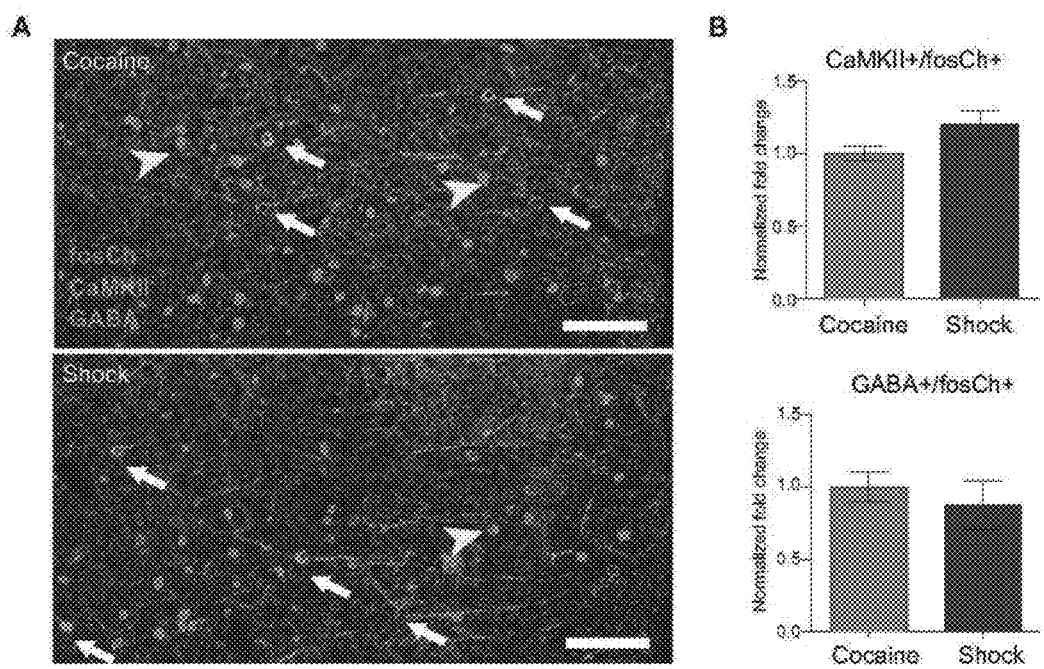
FIG. 9, panels A-B: Additional data showing the use of fosCh for targeting cocaine and shock-activated mPFC populations.

FIG. 9: Use of fosCh for targeting cocaine- and shock-activated mPFC populations. (FIG. 9A) Representative confocal images showing fosCh expression in mPFC sections co-labeled with anti-GABA, and anti-CaMKIIα antibodies as indicated. White arrows indicate fosCh+/CaMKIIα+ neurons. Yellow arrowheads indicate fosCh+/GABAα+ neurons. (FIG. 9B) Quantification revealed no significant difference in the number of CaMKIIα-positive (left) and GABA-positive (right) fosCh cells for cocaine and shock groups. n=10-14 mice per group. Error bars, mean±s.e.m.

Figure 10:
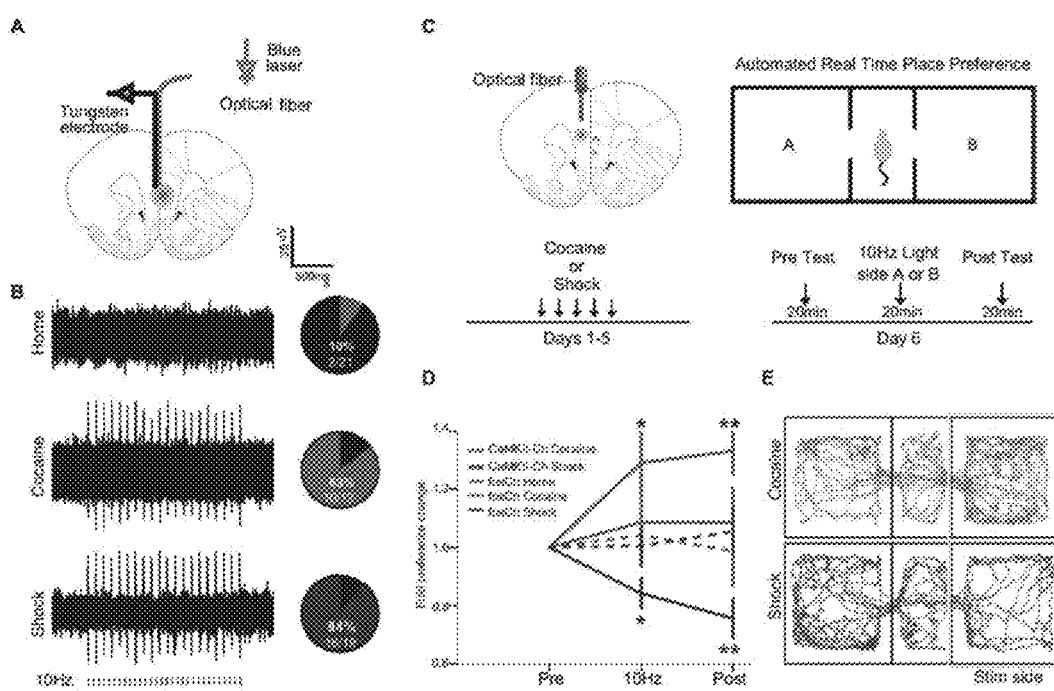
FIG. 10, panels A-E: Schematic showing the placement of electrodes for recording experiments, and data showing the differential behavioral influence of cocaine and shock-activated mPFC populations.

FIG. 10: Differential behavioral influence of cocaine- and shock-activated mPFC populations. (FIG. 10A) Schematic to illustrate the placement of the recording electrode and optical fiber for in vivo recording experiments. The optrode was lowered in 100 µm steps along the dorsal-ventral axis of mPFC. (FIG. 10B) Left, representative extracellular recordings showing neural response to a 10 Hz light train (5 ms pulses for 2 sec, every 5 sec, 5 mW 473 nm blue light, indicated by blue bars). Right, pie charts indicate percentage of recording sites showing light-evoked action potential firing for the home cage (grey), cocaine (red), and shock (blue) groups. (FIG. 10C) Schematic shows the location of the optical fiber positioned above the injection site in green. After 5 days of training, mice were tested by real time place preference test which consisted of 3 consecutive 20-minute trials. (FIG. 10D) Behavioral results plotted as fold-change in preference for the light stimulated side (normalized by initial baseline preference) across each of the trials. n=10-14 per group, *P<0.05, **P<0.01, ANOVA followed by Tukey's multiple comparison test. Error bars, mean±s.e.m. (FIG. 10E) Movement tracking data from representative cocaine- and shock-labeled animals during the light stimulation trial.

To address this question, the real-time place preference paradigm in which 10 Hz light pulse trains were automatically triggered upon entry into one side of a behavioral chamber was employed. Mouse behavior was monitored over 3 consecutive 20-minute trials to quantify place preference, before, during, and after light delivery for reactivation of fosCh-defined neuronal ensembles (FIG. 10C). Additional experimental arms in which expression of ChR2 was driven by the CaMKIIα promoter without link to prior activity was included, to control for the possibility that behavior could be biased by randomly-labeled neurons; in this control arm, virus was titered to target a similar number of mPFC neurons and matched to fosCh expression levels following cocaine or shock exposure (FIGS. 11A-11B). Optogenetic stimulation of these non-activity-specific neuronal populations did not influence place preference, nor were homecage-recruited fosCh-population animals observed to exhibit preference or aversion for the chamber in which the cells were optically activated. Remarkably, however, reactivation of the shock or cocaine-defined fosCh populations induced significant (and opposite-direction) shifts in place preference, with cocaine-exposed mice demonstrating preference, and shock-exposed mice demonstrating aversion, for the photostimulation-paired side (FIGS. 10D-10E; mean preference change at post-test for cocaine: 1.3×+/−0.1, Wilcoxon P=0.0006; for shock: 0.8×+/−0.1, Wilcoxon P=0.002). These data reveal that the activity-defined mPFC neural populations differ not only anatomically and molecularly, but also in functional impact in modulating behavior.

Figure 11:
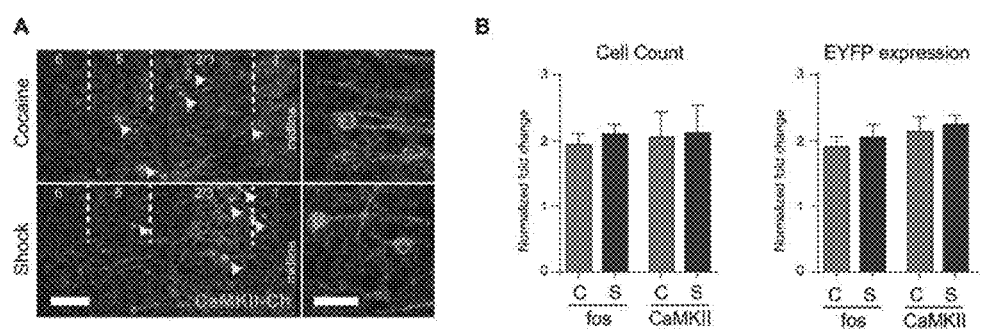
FIG. 11, panels A-B: Additional data showing the differential behavioral influence of cocaine and shock-activated mPFC populations.

FIG. 11: Differential behavioral influence of cocaine- and shock-activated mPFC populations. (FIG. 11A) Representative images showing mPFC expression of CaMKIIα-ChR2 control conditions. Left, two 40× images were stitched together to visualize all cortical lamina. Scale bar=100 µm. Right, high magnification images of individual CaMKIIα-ChR2 neurons. Scale bar=25 µm. (FIG. 11B) Quantification revealed no significant difference in the number of labeled cells (left) or level of EFYP expression (right) between CaMKIIα-ChR2 and fosCh conditions. n=13 mice per group. Error bars, mean±s.e.m.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of preparing a biological specimen for imaging analysis, the method comprising:
   i) fixing the biological specimen with a plurality of hydrogel monomers to produce a hydrogel-fixed specimen;
   ii) clearing the hydrogel-fixed specimen using a non-electrophoretic flow-assisted clearing device to produce a cleared specimen, wherein the clearing is performed by:
      a) immersing the hydrogel-fixed specimen in a buffer in a sample chamber of the flow-assisted clearing device;
      b) flowing the buffer through the hydrogel-fixed specimen by using a buffer circulator, wherein buffer flow through the hydrogel-fixed specimen is unidirectional and sufficient to clear the hydrogel-fixed specimen, wherein the buffer flow direction through the hydrogel-fixed specimen is determined by the buffer circulator; and
   iii) contacting the cleared specimen with a refractive index matching solution prior to imaging analysis.

2. The method of claim 1, wherein the flow-assisted clearing device comprises:
   a sample chamber comprising an inlet and an outlet, wherein the inlet delivers the buffer into the sample chamber and the outlet draws the buffer out of the sample chamber;
   a sample holder, wherein the sample holder can be removably placed inside the sample chamber, and wherein the sample holder allows the buffer to flow through; and
   the buffer circulator.

3. The method of claim 2, wherein the buffer circulator is a temperature-controlled circulator.

4. The method of claim 1, wherein the flow-assisted clearing device comprises:
   a container;
   a sample holder, wherein the sample holder allows the buffer to flow through, and wherein the sample holder can be removably placed inside the container; and
   a buffer circulator.

5. The method of claim 4, wherein the buffer circulator comprises a rotating rod.

6. The method of claim 5, wherein the rotating rod is a magnetic rotating rod and is controlled by an external magnetic field.

7. The method of claim 4, wherein a plurality of flow-assisted clearing devices are arranged in parallel to the buffer circulator.

8. The method of claim 7, wherein each of the plurality of flow-assisted clearing devices clears a plurality of hydrogel-fixed specimens.

9. The method of claim 4, wherein the buffer circulator generates a unidirectional flow of the buffer through the sample holder.

10. The method of claim 1, wherein the flow-assisted clearing device is not an electrophoresis chamber.

11. The method of claim 1, wherein the flow-assisted clearing device further comprises a buffer filter component.

12. The method of claim 11, further comprising passing the buffer through the buffer filter component, wherein the buffer filter component substantially filters out all cleared cellular components from the hydrogel-fixed specimen.

13. The method of claim 12, wherein the buffer is reused in the flow-assisted clearing device after said passing the buffer through the buffer filter component.

14. The method of claim 1, wherein fixing the biological specimen comprises contacting the biological specimen with paraformaldehyde.

15. The method of claim 14, wherein contacting the biological specimen with paraformaldehyde comprises transcardial perfusion.

16. The method of claim 1, wherein the plurality of hydrogel monomers comprise acrylamide.

17. The method of claim 16, wherein the plurality of hydrogel monomers comprise 1% acrylamide.

18. The method of claim 1, wherein clearing the hydrogel-fixed specimen further comprises substantially removing a plurality of cellular components from the hydrogel-fixed specimen.

19. The method of claim 18, wherein the plurality of cellular components comprise lipids.

20. The method of claim 1, wherein clearing the hydrogel-fixed specimen is performed at about 40° C.

21. The method of claim 1, wherein the buffer comprises a Tris buffer and an ionic surfactant.

22. The method of claim 21, wherein the Tris buffer is Tris-Boric buffer.

23. The method of claim 22, wherein the ionic surfactant is sodium dodecyl sulfate.

24. The method of claim 1, wherein the buffer is at about pH 8.5.

25. The method of claim 1, wherein the refractive index matching solution has a refractive index that matches that of the cleared specimen.

26. The method of claim 25, wherein the refractive index matching solution has a refractive index of 1.45.

27. The method of claim 1, wherein the biological specimen is a central nervous system tissue.

28. The method of claim 27, wherein the central nervous system tissue is a whole brain.

29. The method of claim 1, wherein the biological specimen is a whole spinal cord.

* * * * *